United States Patent
Rao et al.

(10) Patent No.: US 9,777,139 B2
(45) Date of Patent: Oct. 3, 2017

(54) REACTIVE ANTIOXIDANTS, ANTIOXIDANT-CONTAINING PREPOLYMERS, AND COMPOSITIONS THEREOF

(71) Applicant: PRC-DeSoto International, Inc., Sylmar, CA (US)

(72) Inventors: Chandra Rao, Valencia, CA (US); Juexiao Cai, Stevenson Ranch, CA (US); Renhe Lin, Stevenson Ranch, CA (US)

(73) Assignee: PRC-DeSoto International, Inc., Sylmar, CA (US)

( * ) Notice: Subject to any disclaimer, the term of this patent is extended or adjusted under 35 U.S.C. 154(b) by 0 days.

(21) Appl. No.: 14/922,280

(22) Filed: Oct. 26, 2015

(65) Prior Publication Data

US 2017/0114208 A1     Apr. 27, 2017

(51) Int. Cl.
| | | |
|---|---|---|
| *C08G 63/02* | (2006.01) | |
| *C08K 5/375* | (2006.01) | |
| *C08K 5/378* | (2006.01) | |
| *C09J 181/02* | (2006.01) | |
| *C09J 5/00* | (2006.01) | |

(52) U.S. Cl.
CPC ............. *C08K 5/375* (2013.01); *C08K 5/378* (2013.01); *C09J 5/00* (2013.01); *C09J 181/02* (2013.01); *C09J 2481/00* (2013.01)

(58) Field of Classification Search
CPC .................................................... C08K 5/375
USPC ......................................................... 525/403
See application file for complete search history.

(56) References Cited

U.S. PATENT DOCUMENTS

| | | | |
|---|---|---|---|
| 4,366,307 A | 12/1982 | Singh et al. | |
| 4,609,762 A | 9/1986 | Morris et al. | |
| 5,225,472 A | 7/1993 | Cameron et al. | |
| 5,270,364 A | 12/1993 | Schwartz et al. | |
| 6,172,179 B1 | 1/2001 | Zook et al. | |
| 6,184,280 B1 | 2/2001 | Shibuta | |
| 6,509,418 B1 | 1/2003 | Zook et al. | |
| 6,525,168 B2 | 2/2003 | Zook et al. | |
| 7,009,032 B2 | 3/2006 | Bojkova et al. | |
| 7,671,145 B2 | 3/2010 | Sawant et al. | |
| 7,879,955 B2 | 2/2011 | Rao et al. | |
| 2005/0010003 A1 | 1/2005 | Sawant et al. | |
| 2006/0270796 A1 | 11/2006 | Sawant et al. | |
| 2007/0270548 A1* | 11/2007 | Bojkova | C08G 18/3234 525/123 |
| 2010/0010133 A1 | 1/2010 | Zook et al. | |
| 2010/0041839 A1 | 2/2010 | Anderson et al. | |
| 2011/0319559 A1 | 12/2011 | Kania et al. | |
| 2012/0234205 A1 | 9/2012 | Hobbs et al. | |
| 2012/0238707 A1 | 9/2012 | Hobbs et al. | |
| 2013/0345371 A1 | 12/2013 | Anderson et al. | |
| 2015/0252230 A1 | 9/2015 | Keledjian et al. | |

FOREIGN PATENT DOCUMENTS

WO     WO 2014/205319 A1     12/2014

OTHER PUBLICATIONS

Marvel et al., "Polymercaptals and Polymercaptols", Journal of American Chemical Society, 1950, vol. 72, p. 2106-2109.
Marvel et al., "A twenty-six-membered cyclic dimercapital", Journal of American Chemical Society, 1954, vol. 76, p. 933-934.
Marvel et al., "Cyclic Cimercapitals and Dimercapitols from Alkylene Dithiols", Journal of American Chemical Society, 1957, vol. 79, p. 986-988.
Steffi Sensfub, "New aspects of the synthesis of polymercapitals", Die Angewandte Macromolecular Chemistry, 1996, vol. 234, p. 191-207.
Steffi Sensfub, "Chain-Cycle Equilibrium in the course of the polycondensation of aldehydes with $\alpha,\omega$-dithiols", Die Angewandte Macromolecular Chemistry,1996, vol. 243, p. 161-176.
Perni, "Amberlyst-15 as a convenient catalyst for chemoselective thioacetalization", Synthetic Communications, 1989, p. 2383-2387.
Kumar et al., Titanium tetrachloride, an efficient and convenient reagent for thioacetalization, Tetrahedron Letters, 1983, vol. 24, No. 12, p. 1289-1292.

* cited by examiner

*Primary Examiner* — Terressa Boykin
(74) *Attorney, Agent, or Firm* — William R. Lambert

(57) ABSTRACT

Reactive antioxidants, antioxidant-containing prepolymers, compositions containing reactive antioxidants and antioxidant-containing prepolymers, methods of synthesizing reactive antioxidants and reactive antioxidant-containing prepolymers and the use of reactive antioxidants and antioxidant-containing prepolymers in aerospace sealant applications are disclosed. Reactive antioxidants and antioxidant-containing prepolymers can be added to a curable composition and react with a curing agent to become incorporated into the cured polymer network. Antioxidant-containing prepolymers have antioxidants incorporated into the backbone of the prepolymer. Cured sealant compositions comprising reactive antioxidants and antioxidant-containing prepolymers exhibit enhanced thermal resistance.

20 Claims, No Drawings

REACTIVE ANTIOXIDANTS, ANTIOXIDANT-CONTAINING PREPOLYMERS, AND COMPOSITIONS THEREOF

FIELD

The present disclosure relates to reactive antioxidants and antioxidant-containing prepolymers, compositions containing reactive antioxidants and/or antioxidant-containing prepolymers, methods of synthesizing reactive antioxidants and/or antioxidant-containing prepolymers, and uses of reactive antioxidants and antioxidant-containing prepolymers in aerospace sealant applications. Reactive antioxidants include compounds containing an antioxidant moiety and groups reactive with prepolymers and/or curing agents. Cured sealant compositions comprising reactive antioxidants and antioxidant-containing prepolymers exhibit enhanced thermal resistance.

BACKGROUND

Sealants useful in aerospace applications must satisfy demanding mechanical, chemical, and environmental requirements. For example, it is desirable that aerospace sealants function over a temperature range such as from about −67° F. to about 400° F. and exhibit fuel resistance. Antioxidants can be added to a polymeric sealant to improve thermal stability. Typical antioxidants are low molecular weight compounds that can be extracted from a cured polymer upon exposure to solvents such as aviation fuel at elevated temperature.

Aerospace sealants containing antioxidants that exhibit enhanced thermal stability are desired.

SUMMARY

Reactive antioxidants are provided, wherein the reactive antioxidants comprise a reactive antioxidant having the structure of Formula (1a), a reactive antioxidant having the structure of Formula (1b), a reactive antioxidant having the structure of Formula (1c), or a combination of any of the foregoing:

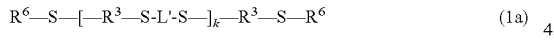
$$R^6-S-[-R^3-S-L'-S-]_k-R^3-S-R^6 \quad (1a)$$

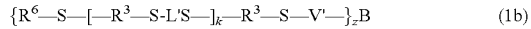
$$\{R^6-S-[-R^3-S-L'S-]_k-R^3-S-V'-\}_zB \quad (1b)$$

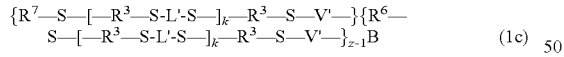
$$\{R^7-S-[-R^3-S-L'-S-]_k-R^3-S-V'-\}\{R^6-S-[-R^3-S-L'-S-]_k-R^3-S-V'-\}_{z-1}B \quad (1c)$$

wherein,
each k is independently 0 to 10, wherein at least one k is not 0;
each $R^6$ is hydrogen or comprises a moiety having a terminal reactive group;
each $R^3$ independently comprises a moiety of Formula (2):

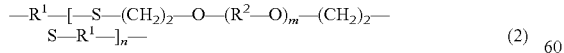
$$-R^1-[-S-(CH_2)_2-O-(R^2-O)_m-(CH_2)_2-S-R^1-]_n- \quad (2)$$

wherein,
n is an integer from 0 to 60;
each $R^1$ independently comprises $C_{2-10}$ alkanediyl, $C_{6-8}$ cycloalkanediyl, $C_{6-10}$ alkanecycloalkanediyl, $C_{5-8}$ heterocycloalkanediyl, $-[(-CHR-)_p-X-]_q(-CHR-)_r-$;
p is an integer from 2 to 6;
q is an integer from 1 to 5;
r is an integer from 2 to 10;
each R independently comprises hydrogen or methyl; and
each X independently comprises —O—, —S—, or —NR—, wherein R comprises hydrogen or methyl;
each $R^2$ independently comprises $C_{1-10}$ alkanediyl, $C_{6-8}$ cycloalkanediyl, $C_{6-14}$ alkanecycloalkanediyl, or $-[(-CHR-)_p-X-]_q-(-CHR-)_r-$, wherein p, q, r, R, and X are as defined for $R^1$;
m is an integer from 0 to 50;
each -L'— is derived from an antioxidant-containing precursor L, wherein the antioxidant-containing precursor L comprises an antioxidant moiety and at least one group reactive with a thiol group;
B represents a core of a z-valent polyfunctionalizing agent $B(-V)_z$ wherein,
z is an integer from 3 to 6;
each —V is a moiety comprising a terminal group reactive with a terminal thiol group;
each —V'— is derived from the reaction of —V with a thiol group; and
$R^7$ is $\{-V'-\}\{R^6-S-[-R^3-S-L'-S-]_k-R^3-S-V'-\}_{z-1}B$.

Reactive antioxidants are provided comprising the reaction product of reactants comprising a polythiol; and an antioxidant-containing precursor comprising at least one group reactive with thiol groups and at least one antioxidant moiety.

Compositions comprising a reactive antioxidant and/or an antioxidant-containing prepolymer of the present disclosure are provided.

Methods of preparing reactive antioxidants are provided, comprising reacting a polythiol and an antioxidant-containing precursor, wherein,
the polythiol comprises a polythiol of Formula (7a), a polythiol of Formula (7b), or a combination thereof:

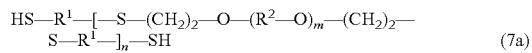
$$HS-R^1-[-S-(CH_2)_2-O-(R^2-O)_m-(CH_2)_2-S-R^1-]_n-SH \quad (7a)$$

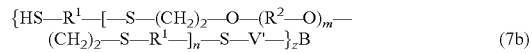
$$\{HS-R^1-[-S-(CH_2)_2-O-(R^2-O)_m-(CH_2)_2-S-R^1-]_n-S-V'-\}_zB \quad (7b)$$

wherein:
each $R^1$ independently comprises $C_{2-10}$ alkanediyl, $C_{6-8}$ cycloalkanediyl, $C_{6-10}$ alkanecycloalkanediyl, $C_{5-8}$ heterocycloalkanediyl, or $-[(-CHR-)_p-X-]_q-(-CHR-)_r-$, wherein:
p is an integer from 2 to 6;
q is an integer from 1 to 5;
r is an integer from 2 to 10;
each R independently comprises hydrogen or methyl; and
each X independently comprises —O—, —S—, or —NR—, wherein R is selected from hydrogen and methyl;
each $R^2$ independently comprises $C_{1-10}$ alkanediyl, $C_{6-8}$ cycloalkanediyl, $C_{6-14}$ alkanecycloalkanediyl, or $-[(-CHR-)_p-X-]_q-(CHR-)_r-$, wherein p, q, r, R, and X are as defined for $R^1$;
m is an integer from 0 to 50;
n is an integer from 0 to 60;
B represents a core of a z-valent polyfunctionalizing agent $B(-V)_z$ wherein:
z is an integer from 3 to 6;
each V is a moiety comprising a terminal group reactive with terminal thiol groups; and
each —V'— is derived from the reaction of —V with a thiol; and the antioxidant-containing precursor comprises at least one group reactive with thiol groups; and an antioxidant moiety.

Methods of sealing a part a provided, comprising preparing a curable composition comprising a sealant composition provided by the present disclosure; applying the curable composition to a part; and curing the curable composition to seal the part.

Reference is now made to compounds, compositions and methods according to the present invention. The disclosed embodiments are not intended to be limiting of the claims. To the contrary, the claims are intended to cover all alternatives, modifications, and equivalents.

DETAILED DESCRIPTION

For purposes of the following description, it is to be understood that embodiments provided by the present disclosure may assume various alternative variations and step sequences, except where expressly specified to the contrary. Moreover, other than in the examples, or where otherwise indicated, all numbers expressing, for example, quantities of ingredients used in the specification and claims are to be understood as being modified in all instances by the term "about." Accordingly, unless indicated to the contrary, the numerical parameters set forth in the following specification and attached claims are approximations that may vary depending upon the desired properties to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

Also, it should be understood that any numerical range recited herein is intended to include all sub-ranges encompassed therein. For example, a range of "1 to 10" is intended to include all sub-ranges between (and including) the recited minimum value of about 1 and the recited maximum value of about 10, that is, having a minimum value equal to or greater than about 1 and a maximum value of equal to or less than about 10. Also, in this application, the use of "or" means "and/or" unless specifically stated otherwise, even though "and/or" may be explicitly used in certain instances.

Furthermore, when reference is made to a chemical group defined, for example, by a number of carbon atoms, the chemical group is intended to include the all sub-ranges of carbon atoms and a specific number of carbon atoms. For example, a $C_{2-10}$ alkanediyl includes a $C_{2-4}$ alkanediyl, $C_{5-7}$ alkanediyl, and other sub-ranges, and a $C_2$ alkanediyl, a $C_6$ alkanediyl, and other specific number of carbon atoms.

A dash ("-") that is not between two letters or symbols is used to indicate a point of covalent bonding for a substituent or between two atoms. For example, the chemical group —$CONH_2$ is covalently bonded to another chemical moiety through the carbon atom.

"Alkanearene" refers to a hydrocarbon group having one or more aryl and/or arenediyl groups and one or more alkyl and/or alkanediyl groups, where aryl, arenediyl, alkyl, and alkanediyl are defined herein. Each aryl and/or arenediyl group(s) can be $C_{6-12}$, $C_{6-10}$, phenyl or benzenediyl. Each alkyl and/or alkanediyl group(s) can be $C_{1-6}$, $C_{1-4}$, $C_{1-3}$, methyl, methanediyl, ethyl, or ethane-1,2-diyl. An alkanearene group can be $C_{4-18}$ alkanearene, $C_{4-16}$ alkanearene, $C_{4-12}$ alkanearene, $C_{4-8}$ alkanearene, $C_{6-12}$ alkanearene, $C_{6-10}$ alkanearene, or $C_{6-9}$ alkanearene. Examples of alkanearene groups include diphenyl methane.

"Alkanearenediyl" refers to a diradical of an alkanearene group. An alkanearenediyl group can be $C_{4-18}$ alkanearenediyl, $C_{4-16}$ alkanearenediyl, $C_{4-12}$ alkanearenediyl, $C_{4-8}$ alkanearenediyl, $C_{6-12}$ alkanearenediyl, $C_{6-10}$ alkanearenediyl, or $C_{6-9}$ alkanearenediyl. Examples of alkanearenediyl groups include diphenyl methane-4,4'-diyl.

"Alkanediyl" refers to a diradical of a saturated, branched or straight-chain, acyclic hydrocarbon group, having, for example, from 1 to 18 carbon atoms ($C_{1-18}$), from 1 to 14 carbon atoms ($C_{1-14}$), from 1 to 6 carbon atoms ($C_{1-6}$), from 1 to 4 carbon atoms ($C_{1-4}$), or from 1 to 3 hydrocarbon atoms ($C_{1-3}$). It will be appreciated that a branched alkanediyl has a minimum of three carbon atoms. An alkanediyl can be $C_{2-14}$ alkanediyl, $C_{2-10}$ alkanediyl, $C_{2-8}$ alkanediyl, $C_{2-6}$ alkanediyl, $C_{2-4}$ alkanediyl, or $C_{2-3}$ alkanediyl. Examples of alkanediyl groups include methane-diyl (—$CH_2$—), ethane-1,2-diyl (—$CH_2CH_2$—), propane-1,3-diyl and iso-propane-1,2-diyl (e.g., —$CH_2CH_2CH_2$— and —$CH(CH_3)CH_2$—), butane-1,4-diyl (—$CH_2CH_2CH_2CH_2$—), pentane-1,5-diyl (—$CH_2CH_2CH_2CH_2CH_2$—), hexane-1,6-diyl (—$CH_2CH_2CH_2CH_2CH_2CH_2$—), heptane-1,7-diyl, octane-1,8-diyl, nonane-1,9-diyl, decane-1,10-diyl, dodecane-1,12-diyl, and the like.

"Alkanecycloalkane" refers to a saturated hydrocarbon group having one or more cycloalkyl and/or cycloalkanediyl groups and one or more alkyl and/or alkanediyl groups, where cycloalkyl, cycloalkanediyl, alkyl, and alkanediyl are defined herein. Each cycloalkyl and/or cycloalkanediyl group(s) can be $C_{3-6}$, $C_{5-6}$, cyclohexyl or cyclohexanediyl. Each alkyl and/or alkanediyl group(s) can be $C_{1-6}$, $C_{1-4}$, $C_{1-3}$, methyl, methanediyl, ethyl, or ethane-1,2-diyl. An alkanecycloalkane group can be $C_{4-18}$ alkanecycloalkane, $C_{4-16}$ alkanecycloalkane, $C_{4-12}$ alkanecycloalkane, $C_{4-8}$ alkanecycloalkane, $C_{6-12}$ alkanecycloalkane, $C_{6-10}$ alkanecycloalkane, or $C_{6-9}$ alkanecycloalkane. Examples of alkanecycloalkane groups include 1,1,3,3-tetramethylcyclohexane and cyclohexylmethane.

"Alkanecycloalkanediyl" refers to a diradical of an alkanecycloalkane group. An alkanecycloalkanediyl group can be $C_{4-18}$ alkanecycloalkanediyl, $C_{4-16}$ alkanecycloalkanediyl, $C_{4-12}$ alkanecycloalkanediyl, $C_{4-8}$ alkanecycloalkanediyl, $C_{6-12}$ alkanecycloalkanediyl, $C_{6-10}$ alkanecycloalkanediyl, or $C_{6-9}$ alkanecycloalkanediyl. Examples of alkanecycloalkanediyl groups include 1,1,3,3-tetramethylcyclohexane-1,5-diyl and cyclohexylmethane-4,4'-diyl.

"Alkenyl" group refers to a group having the structure —$CR=CR_2$ where the alkenyl group is a terminal group and is bonded to a larger molecule. In such embodiments, each R may be selected from, for example, hydrogen and $C_{1-3}$ alkyl. Each R can be hydrogen and an alkenyl group has the structure —$CH=CH_2$.

"Alkoxy" refers to a —OR group where R is alkyl as defined herein. Examples of alkoxy groups include methoxy, ethoxy, n-propoxy, isopropoxy, and n-butoxy. An alkoxy group can be $C_{1-8}$ alkoxy, $C_{1-6}$ alkoxy, $C_{1-4}$ alkoxy, or $C_{1-3}$ alkoxy.

"Alkyl" refers to a mono-radical of a saturated, branched or straight-chain, acyclic hydrocarbon group having, for example, from 1 to 20 carbon atoms, from 1 to 10 carbon atoms, from 1 to 6 carbon atoms, from 1 to 4 carbon atoms, or from 1 to 3 carbon atoms. It will be appreciated that a branched alkyl has a minimum of three carbon atoms. An alkyl group can be $C_{1-6}$ alkyl, $C_{1-4}$ alkyl, or $C_{1-3}$ alkyl. Examples of alkyl groups include methyl, ethyl, n-propyl, iso-propyl, n-butyl, iso-butyl, tert-butyl, n-hexyl, n-decyl, and tetradecyl. An alkyl group can be $C_{1-6}$ alkyl, $C_{1-4}$ alkyl, or $C_{1-3}$ alkyl. It will be appreciated that a branched alkyl has at least three carbon atoms.

"Antioxidant-containing precursor" refers to a chemical compound that includes an antioxidant moiety and a moiety reactive with another compounds. For example, an antioxidant-containing precursor may have the structure: which comprises the antioxidant moiety:

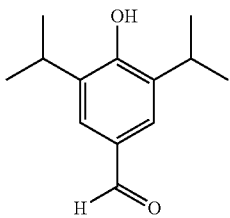

and an aldehyde moiety —CH=O,

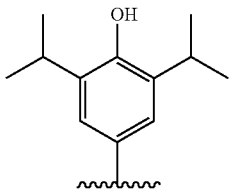 [SMILES: *c1cc(C(C)C)c(O)c(C(C)C)c1]

which is reactive with thiol groups.

"A moiety derived from an antioxidant-containing precursor" refers to a moiety that results from the reaction of an antioxidant-containing precursor with another compound.

"Reactive antioxidant" refers to a compound that contains at least one antioxidant moiety and that has reactive functional groups such as reactive terminal groups capable of reacting with other functional groups to form, for example, a cured polymer network. A reactive antioxidant can have, for example from 2 to 6 functional groups. The functional groups can be, for example, thiol groups, epoxy groups, alkenyl groups, hydroxyl groups, isocyanate groups, or Michael acceptor groups. A reactive antioxidant can also encompass antioxidant-containing sulfur-containing prepolymers including thiol-terminated antioxidant-containing prepolymers and thiol-terminated antioxidant-containing polythioethers. In general, reactive antioxidants refer to lower molecular weight compounds and antioxidant-containing prepolymers refer to higher molecular weight compounds. Reactive antioxidants may be used to prepare antioxidant-containing prepolymers. In compositions, reactive antioxidants and antioxidant-containing prepolymers may be used independently or in combination. The terms reactive antioxidant and antioxidant-containing prepolymer are used interchangeably.

"Cycloalkanediyl" refers to a diradical saturated monocyclic or polycyclic hydrocarbon group. An cycloalkanediyl group can be $C_{3-12}$ cycloalkanediyl, $C_{3-8}$ cycloalkanediyl, $C_{3-6}$ cycloalkanediyl, or, $C_{5-6}$ cycloalkanediyl. Examples of cycloalkanediyl groups include cyclohexane-1,4-diyl, cyclohexane-1,3-diyl, and cyclohexane-1,2-diyl.

"Cycloalkyl" refers to a saturated monocyclic or polycyclic hydrocarbon monoradical group. A cycloalkyl group is $C_{3-12}$ cycloalkyl, $C_{3-8}$ cycloalkyl, $C_{3-6}$ cycloalkyl, or $C_{5-6}$ cycloalkyl.

"Heteroalkanediyl" refers to an alkanediyl group in which one or more of the carbon atoms are replaced with a heteroatom, such as N, O, S, or P. In a heteroalkanediyl, a heteroatom can be selected from N and O.

"Heteroalkanearenediyl" refers to an alkanearenediyl group in which one or more of the carbon atoms are replaced with a heteroatom, such as N, O, S, or P. In a heteroalkanearenediyl, a heteroatom can be selected from N and O.

"Heterocycloalkanediyl" refers to a cycloalkanediyl group in which one or more of the carbon atoms are replaced with a heteroatom, such as N, O, S, or P. In a heterocycloalkanediyl, a heteroatom can be selected from N and O.

"Michael acceptor group" refers to substituted alkene/alkyne compounds in which at least one alkene/alkyne group is directly attached to one or more electron-withdrawing groups such as carbonyl (—CO), nitro (—$NO_2$), nitrile (—CN), alkoxycarbonyl (—COOR), phosphonate (—PO$(OR)_2$), trifluoromethyl (—$CF_3$), sulfonyl (—$SO_2$—), trifluoromethanesulfonyl (—$SO_2CF_3$), p-toluenesulfonyl (—$SO_2$—$C_6H_4$—$CH_3$), etc. Types of compounds that function as Michael acceptor are vinyl ketones, quinones, nitroalkenes, acrylonitriles, acrylates, methacrylates, cyanoacrylates, acrylamides, maleimides, dialkyl vinylphosphonate and vinylsulfones. Other examples of Michael acceptors are disclosed in Mather et al., *Prog. Polym. Sci.* 2006, 31, 487-531. Michael acceptor compounds having more than one Michael acceptor group are also well known. Examples include diacrylates such as ethylene glycol diacrylate and diethylene glycol diacrylate, dimethacrylates such as ethylene glycol methacrylate and diethylene glycol methacrylate, bismaleimides such as N,N'-(1,3-phenylene)dimaleimide and 1,1'-(methylenedi-4,1-phenylene)bismaleimide, vinylsulfones such as divinyl sulfone and 1,3-bis(vinylsulfonyl)-2-propanol, etc. A Michael acceptor group can have the structure of Formula (11a) or Formula (11b):

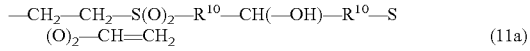 (11a)

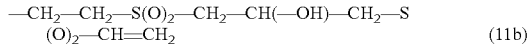 (11b)

where each $R^{10}$ is independently selected from $C_{1-3}$ alkanediyl and substituted $C_{1-3}$ alkanediyl, wherein the one or more substituent groups is —OH.

An "oxyalkanediyl group" refers to an alkanediyl group in which one or more of the —$CH_2$— groups is replaced with an ether —O— group.

A "polyalkoxysilyl group" refers to a group having Formula (12):

 (12)

where p is selected from 0, 1, and 2; and each $R^4$ is independently selected from $C_{1-4}$ alkyl. In a polyalkoxysilyl group, p can be 0, p can be 1, or p can be 2. In a polyalkoxysilyl group, each $R^4$ can independently be selected from ethyl and methyl. In a polyalkoxysilyl group, each $R^4$ can be ethyl, or each $R^4$ can be methyl. In a polyalkoxysilyl group, the polyalkoxysilyl group can selected from —Si(—$OCH_2CH_3$)$_3$, —Si(—$OCH_3$)$_3$, —Si(—$CH_3$)(—$OCH_3$)$_2$, —Si(—$CH_3$)$_2$(—$OCH_3$), —Si(—$CH_3$)(—$OCH_2CH_3$)$_2$, —Si(—$CH_3$)$_2$(—$OCH_2CH_3$), —Si(—$CH_2CH_3$)(—$OCH_3$), and —Si(—$CH_2CH_3$)$_2$(—$OCH_3$).

"Substituted" refers to a group in which one or more hydrogen atoms are each independently replaced with the same or different substituent(s). A substituent can be selected from halogen, —S(O)$_2$OH, S(O)$_2$, —SH, —SR where R is C$_{1-6}$ alkyl, —COOH, —NO$_2$, —NR$_2$ where each R is independently selected from hydrogen and C$_{1-3}$ alkyl, —CN, —C(H)=O, —C(=O)—, C$_{1-6}$ alkyl, —CF$_3$, —OH, phenyl, C$_{2-6}$ heteroalkyl, C$_{5-6}$ heteroaryl, C$_{1-6}$ alkoxy, and —COR where R is C$_{1-6}$ alkyl. For example, a substituent can be chosen from —OH, —NH$_2$, and C$_{1-3}$ alkyl.

As used herein, "polymer" refers to oligomers, homopolymers, and copolymers. Unless stated otherwise, molecular weights are number average molecular weights for polymeric materials indicated as "$M_n$," as determined, for example, by gel permeation chromatography using a polystyrene standard in an art-recognized manner.

A "sulfur-containing prepolymer" can be any polymer having at least one sulfur atom in the repeating unit, including, but not limited to, polymeric thiols, polythiols, thioethers, polythioethers, sulfur-containing polyformals, and polysulfides. A "thiol," as used herein, refers to a compound comprising a thiol or mercaptan group, that is, an "SH" group, either as the sole functional group or in combination with other functional groups, such as hydroxyl groups, as is the case with, for example, thioglycerols. A polythiol refers to such a compound having more than one SH group, such as a dithiol or higher functionality thiol. Such groups are typically terminal and/or pendant such that they have an active hydrogen that is reactive with other functional groups. A polythiol can comprise both a terminal and/or pendant sulfur (—SH) and a non-reactive sulfur atom (—S— or —S—S—). Thus, the term polythiol generally encompasses polythioethers and polysulfides.

The term polysulfide refers to a polymer that contains one or more sulfide linkages, i.e., —Sx-linkages, where x is from 2 to 4, in the polymer backbone and/or in pendant positions on the polymer chain. A polysulfide polymer can have two or more sulfur-sulfur linkages. Suitable polysulfides are commercially available, for example, from Akzo Nobel and Toray Fine Chemicals under the names Thiokol-LP and Thioplast®. Thioplast® products are available in a wide range of molecular weights ranging, for example, from less than 1,100 to over 8,000, with molecular weight being the average molecular weight in grams per mole. In some cases, the polysulfide has a number average molecular weight of 1,000 Daltons to 4,000 Daltons.

Sulfur-containing polyformal prepolymers useful in aerospace sealant applications are disclosed, for example, in U.S. Application Publication No. 2012/0234205 and in U.S. Application Publication No. 2012/0238707.

Reference is now made to certain reactive antioxidants and antioxidant prepolymers such as metal ligand-containing polythioethers, compositions thereof, and methods of synthesis. The disclosed embodiments are not intended to be limiting of the claims. To the contrary, the claims are intended to cover all alternatives, modifications, and equivalents.

To enhance the thermal resistance of cured aerospace sealants, antioxidants can be covalently bound to a cured polymeric network, which prevents extraction of the antioxidant upon exposure to aviation fuel at high temperature. Antioxidants can be incorporated into a cured polymer network by adding reactive antioxidants to a sealant formulation where the reactive antioxidants are reactive with the prepolymer binder or with the curing agent. Alternatively, an antioxidant-containing precursor can be incorporated into the backbone of a prepolymer used to form a sealant composition.

Antioxidant-Containing Precursors

Antioxidants useful for improving the thermal and environmental stability of cured coatings and sealants are known. General classes of antioxidants include sterically hindered phenols, hindered amines, and benzofuranones.

Suitable antioxidants-containing precursor for use in preparing reactive antioxidants and antioxidant-containing prepolymers provided by the present disclosure include those having at least one antioxidant moiety and at least one group reactive with thiol groups. The antioxidant-containing precursor may include one group that is reactive with two thiol groups or more than one group reactive with a thiol group.

For example, an antioxidant-containing precursor may contain an aldehyde group that is reactive with two thiol groups, and the antioxidant moiety can comprise a substituted benzaldehyde. A substituted benzaldehyde can include 3,5-di-tert-butyl-4-hydroxybenzaldehyde, 2,3,4-trihydroxybenzaldehyde, or a combination thereof.

Reactive Antioxidants

Reactive antioxidants provided by the present disclosure include compounds comprising at least one antioxidant moiety and at least two reactive groups. The at least two reactive groups may be reactive with another component of a sealant composition such as a prepolymer or a curing agent. The reactive groups of the reactive antioxidant can covalently bind the antioxidant moiety to the cured polymer network and thereby inhibit extraction of the antioxidant during exposure of the sealant to aviation fuel and high temperature. A reactive antioxidant may be added to a sealant formulation or may serve as a monomer precursor to prepare an antioxidant-containing prepolymer.

Reactive antioxidants provided by the present disclosure can comprise a reactive antioxidant having the structure of Formula (1a), a reactive antioxidant having the structure of Formula (1b), a reactive antioxidant having the structure of Formula (1c), or a combination of any of the foregoing:

$$R^6—S—[—R^3—S\text{-}L'\text{-}S—]_k—R^3—S—R^6 \quad (1a)$$

$$\{R^6—S—[—R^3—S\text{-}L'S—]_k—R^3—S—V'—\}_zB \quad (1b)$$

$$\{R^7—S—[—R^3—S\text{-}L'\text{-}S—]_k—R^3—S—V'—\}\{R^6—S—[—R^3—S\text{-}L'\text{-}S—]_k—R^3—S—V'—\}_{z-1}B \quad (1c)$$

wherein,
  each k is independently 0 to 10, wherein at least one k is not 0;
  each R$^6$ is hydrogen or comprises a moiety having a terminal reactive group;
  each R$^3$ independently comprises aa moiety of Formula (2):

$$—R^1—[—S—(CH_2)_2—O—(R^2—O)_m—(CH_2)_2—S—R^1—]_n— \quad (2)$$

wherein,
  n is an integer from 0 to 60;
  each R$^1$ independently comprises C$_{2-10}$ alkanediyl, C$_{6-8}$ cycloalkanediyl, C$_{6-10}$ alkanecycloalkanediyl, C$_{5-8}$ heterocycloalkanediyl, —[(—CHR—)$_p$—X—]$_q$(—CHR—)$_r$—;
  p is an integer from 2 to 6;
  q is an integer from 1 to 5;
  r is an integer from 2 to 10;

each R independently comprises hydrogen or methyl; and each X independently comprises —O—, —S—, or —NR—, wherein R comprises hydrogen or methyl;

each $R^2$ independently comprises $C_{1-10}$ alkanediyl, $C_{6-8}$ cycloalkanediyl, $C_{6-14}$ alkanecycloalkanediyl, or —[(—CHR—)$_p$—X—]$_q$—(—CHR—)$_r$—, wherein p, q, r, R, and X are as defined for $R^1$;

m is an integer from 0 to 50;

each -L'- is derived from an antioxidant-containing precursor L, wherein the antioxidant-containing precursor L comprises an antioxidant moiety and at least one group reactive with a thiol group;

B represents a core of a z-valent polyfunctionalizing agent B(—V)$_z$ wherein, z is an integer from 3 to 6;

each —V is a moiety comprising a terminal group reactive with a terminal thiol group;

each —V'— is derived from the reaction of —V with a thiol group; and $R^7$ is $\{$—V'—$\}\{R^6$—S—[—$R^3$—S-L'-S—]$_k$—$R^3$—S—V'—$\}_{z-1}$B.

In reactive antioxidants of Formula (1a)-(1c), each $R^1$ can be —[—(CHR)$_p$—X—]$_q$—(CHR)$_r$—.

In reactive antioxidants of Formula (1a)-(1c), X can be selected from —O— and —S—, and thus —[—(CHR)$_p$—X—]$_q$—(CHR)$_r$— can be —[(—CHR—)$_p$—O—]$_q$—(CHR)$_r$—, —[(CHR)$_2$—)$_p$—S—]$_q$—(CHR)$_r$—, —[(—CH$_2$—)$_2$—O—]$_q$—(CH$_2$)$_2$—, or —[(CH$_2$)$_2$—S—]$_q$—(CH$_2$)$_2$—. P and r can be equal, such as both p and r can be 2, 3, or 4.

In reactive antioxidants of Formula (1a)-(1c), each $R^1$ can be selected from $C_{2-6}$ alkanediyl and —[—(CHR)$_p$—X—]$_q$—(CHR)$_r$—.

In reactive antioxidants of Formula (1a)-(1c), each $R^1$ can be —[—(CHR)$_p$—X—]$_q$—(CHR)$_r$—, and X can be —O—, or X can be —S—.

In reactive antioxidants of Formula (1a)-(1c), each $R^1$ can be —[—(CHR)$_p$—X—]$_q$—(CHR)$_r$—, p can be 2, r can be 2, q can be 1, and X can be —S—; or p can be 2, q can be 2, r can be 2, and X can be —O—; or p can be 2, r can be 2, q can be 1, and X can be —O—.

In reactive antioxidants of Formula (1a)-(1c), each $R^1$ can be —[—(CHR)$_p$—X—]$_q$—(CHR)$_r$—, each R can be hydrogen, or at least one R can be methyl.

In reactive antioxidants of Formula (1a)-(1c), each $R^1$ be derived from dimercaptodioxaoctane (DMDO) or each $R^1$ is derived from dimercaptodiethylsulfide (DMDS).

In reactive antioxidants of Formula (1a)-(1c), each $R^1$ can be —[(CH$_2$)$_2$—O—]$_2$—(CH$_2$)$_2$—.

In reactive antioxidants of Formula (1a)-(1c), each p can independently be selected from 2, 3, 4, 5, and 6; or each p can be the same and can be 2, 3, 4, 5, or 6.

In reactive antioxidants of Formula (1a)-(1c), each r can be selected from 2, 3, 4, 5, 6, 7, and 8.

In reactive antioxidants of Formula (1a)-(1c), each q can be selected from 1, 2, 3, 4, and 5.

In reactive antioxidants of Formula (1a)-(1c), each m can independently be an integer from 1 to 3. Each m can be the same such as 0, 1, 2, or 3.

In reactive antioxidants of Formula (1a)-(1c), n can be an integer from 0 to 30, an integer from 0 to 20, an integer from 0 to 10, or an integer from 0 to 5. In addition, n can be any integer from 0 to 60. In reactive antioxidants of Formula (1a)-(1c), n can be 0, 1, 2, 3, 4, 5, 6, 7, 8, 9, or 10.

In reactive antioxidants of Formula (1a)-(1c), when n is 0, then $R^3$ is —$R^1$—.

In reactive antioxidants of Formula (1a)-(1c), each $R^6$ can be hydrogen and the reactive antioxidants of Formula (1a)-(1c) are thiol-terminated.

In reactive antioxidants of Formula (1a)-(1c), each $R^6$ can comprise a terminal thiol, alkenyl, hydroxyl, amine, epoxy, isocyanate, polyalkoxysilyl, or Michael acceptor group.

In reactive antioxidants of Formula (1a)-(1c), at least one k is not 0. In other words, k is selected such that a reactive antioxidant of Formula (1a)-(1c) comprises at least one antioxidant moiety. In divalent reactive antioxidants of Formula (1a), k is at least 1, such as 1, 2, 3, or 4, an integer from 1 to 6, or an integer from 1 to 3. In reactive antioxidants having a functionality greater than 2, such as from 3 to 6 as represented by reactive antioxidants of Formula (1b) and Formula (1c), at least one branch of the polyfunctional reactive antioxidant comprises at least one antioxidant moiety. The other branches may or may not comprise at least one antioxidant moiety.

In reactive antioxidants of Formula (1a)-(1c), n can be 0, each $R^6$ can be hydrogen, and each $R^1$ can be —((CH$_2$)$_2$—O—)$_2$—(CH$_2$)$_2$—.

In reactive antioxidants of Formula (1a)-(1c), n can be 0, and then $R^3$ is $R^1$. For example, reactive antioxidants provided by the present disclosure include reactive antioxidants of Formula (1a'), Formula (1b'), Formula (1c'), and combinations of any of the foregoing:

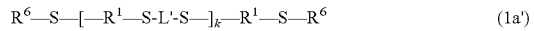

$R^6$—S—[—$R^1$—S-L'-S—]$_k$—$R^1$—S—$R^6$  (1a')

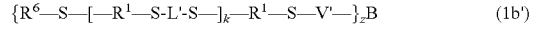

$\{R^6$—S—[—$R^1$—S-L'-S—]$_k$—$R^1$—S—V'—$\}_z$B  (1b')

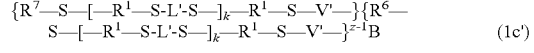

$\{R^7$—S—[—$R^1$—S-L'-S—]$_k$—$R^1$—S—V'—$\}\{R^6$—S—[—$R^1$—S-L'-S—]$_k$—$R^1$—S—V'—$\}^{z-1}$B  (1c')

where k, z, $R^1$, $R^6$, L', V', and B are defined as for reactive antioxidants of Formula (1a)-(1c), and $R^7$ is $\{$—V'—$\}\{R^6$—S—[—$R^1$—S-L'-S—]$_k$—$R^1$—S—V'—$\}_{z-1}$B.

In reactive antioxidants of Formula (1a')-(1c'), —S—$R^1$—S— can be derived from a dithiol having the structure of Formula (3):

HS—$R^1$—SH  (3)

wherein $R^1$ comprises $C_{2-6}$ alkanediyl, $C_{6-8}$ cycloalkanediyl, $C_{6-10}$ alkanecycloalkanediyl, $C_{5-8}$ heterocycloalkanediyl, and —[—(CHR)$_p$—X—]$_q$—(CHR)$_r$—; wherein, each R is independently selected from hydrogen and methyl;

each X is independently selected from —O—, —S—, and —NR— wherein R is selected from hydrogen and methyl;

p is an integer from 2 to 6;

q is an integer from 1 to 5; and r is an integer from 2 to 10.

Examples of suitable dithiols of Formula (3) include, for example, 1,2-ethanedithiol, 1,2-propanedithiol, 1,3-propanedithiol, 1,3-butanedithiol, 1,4-butanedithiol, 2,3-butanedithiol, 1,3-pentanedithiol, 1,5-pentanedithiol, 1,6-hexanedithiol, 1,3-dimercapto-3-methylbutane, dipentenedimercaptan, ethylcyclohexyldithiol (ECHDT), dimercaptodiethylsulfide, methyl-substituted dimercaptodiethylsulfide, dimethyl-substituted dimercaptodiethylsulfide, dimercaptodioxaoctane, 1,5-dimercapto-3-oxapentane, and a combination of any of the foregoing. A polythiol may have one or more pendant groups selected from a lower (e.g., $C_{1-6}$) alkyl group, a lower alkoxy group, and a hydroxy group. Suitable alkyl pendant groups include, for example, $C_{1-6}$ linear alkyl, $C_{3-6}$ branched alkyl, cyclopentyl, and cyclohexyl.

Other examples of suitable dithiols include dimercaptodiethylsulfide (DMDS) (in a dithiol of Formula (3), $R^1$ is $-[(-CH_2-)_p-X-]_q-(CH_2)_r-$, wherein p is 2, r is 2, q is 1, and X is $-S-$); dimercaptodioxaoctane (DMDO) (in a dithiol of Formula (3), $R^1$ is $-[(-CH_2-)_p-X-]_q-(CH_2)_r-$, wherein p is 2, q is 2, r is 2, and X is $-O-$); and 1,5-dimercapto-3-oxapentane (in a dithiol of Formula (3), $R^1$ is $-[(-CH_2-)_p-X-]_q-(CH_2)_r-$, wherein p is 2, r is 2, q is 1, and X is $-O-$). It is also possible to use dithiols that include both a heteroatom in the carbon backbone and a pendant alkyl group, such as a pendant methyl group. Such compounds include, for example, methyl-substituted DMDS, such as $HS-CH_2CH(CH_3)-S-CH_2CH_2-SH$, $HS-CH(CH_3)CH_2-S-CH_2CH_2-SH$ and dimethyl substituted DMDS, such as $HS-CH_2CH(CH_3)-S-CHCH_3CH_2-SH$ and $HS-CH(CH_3)CH_2-S-CH_2CH(CH_3)-SH$.

In reactive antioxidants of Formula (1a)-(1c), $R^6$ can be hydrogen in which case reactive antioxidants provided by the present disclosure can have the structure of Formula (1d), Formula (1e), Formula (f), or a combination of any of the foregoing:

  (1d)

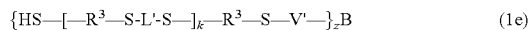  (1e)

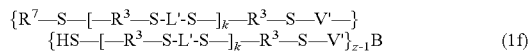  (1f)

where $R^3$, L', V', B, k, and z are defined as for Formula (1a)-(1c); and $R^7$ is $\{-V'-\}\{HS-[-R^3-S-L'-S-]_k-R^3-S-V'-\}_{z-1}B$.

In reactive antioxidants of Formula (1d)-(1f), $R^6$ can be hydrogen in which case reactive antioxidants provided by the present disclosure are thiol-terminated reactive antioxidants and can have the structure of Formula (1d'), Formula (1e'), Formula (1f'), or a combination of any of the foregoing:

  (1d')

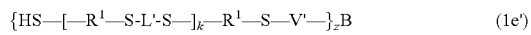  (1e')

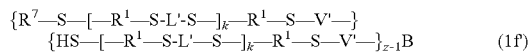  (1f')

where $R^1$, L', V', B, k, and z are defined as for Formula (1a)-(1c); and $R^7$ is $\{-V'-\}\{HS-[-R^1-S-L'-S-]_k-R^1-S-V'-\}_{z-1}B$.

In reactive antioxidants of Formula (1a)-(1c) and (1a')-(1c'), $R^6$ can comprise a reactive terminal group appropriate for a particular curing chemistry. For example, $R^6$ can comprise a terminal thiol group ($-SH$), an alkenyl group ($-CH=CH_2$), an isocyanate group ($-N=C=O$), an epoxy group, an amine group ($-NH_2$), a hydroxyl group ($-OH$), a polyalkoxysilyl group, or a Michael acceptor group. Reactive antioxidants having terminal groups other than thiol groups can also be referred to as terminal-modified reactive antioxidants or capped reactive antioxidants. Terminal-modified reactive antioxidants can be prepared, for example, by reacting a thiol-terminated reactive antioxidant of Formula (1d)-(1f) and (1d')-(1cf') with a compound comprising a group that is reactive with a thiol group and a suitable terminal group such as an alkenyl group, an isocyanate group, an epoxy group, an amine group, a hydroxyl group, a polyalkoxysilyl group, or a Michael acceptor group. Methods for preparing terminal-modified compounds from thiol-terminated precursors are disclosed, for example, in U.S. Application Publication No. 2011/0319559 and U.S. Pat. No. 6,172,179, each of which is incorporated by reference in its entirety. The preparation of terminal-modified sulfur-containing polythioethers is known in the art. For example, isocyanate-terminated polythioethers are disclosed in U.S. application Ser. No. 14/200,687 filed on Mar. 7, 2014, polyalkoxysilyl-terminated polythioethers are disclosed in U.S. application Ser. No. 14/200,687 filed on Mar. 7, 2014, alkenyl-terminated polythioethers are disclosed in U.S. Application Publication No. 2006/0270796; and epoxy-terminated polythioethers are disclosed in U.S. Application Publication No. 2005/0010003, each of which is incorporated by reference in its entirety.

The structure $\{-V'-\}_zB$ in reactive antioxidants of Formula (1b), 1(c), (1b'), (1c'), (1e), (1f), (1e'), and (1f') can be derived from the reaction of a polyfunctionalizing agent $\{V-\}_zB$ with a polythiol such as a dithiol. V— can comprise a terminal group that is reactive with a thiol group. For example V— may comprise a terminal alkenyl group, epoxy group, or Michael acceptor group.

Suitable polyfunctionalizing agents $\{V-\}_zB$ include trifunctional compounds where z is 3. Suitable trifunctionalizing agents include, for example, triallyl cyanurate (TAC) as disclosed, for example, in U.S. Publication No. 2010/0010133, and isocyanurates such as triallyl isocyanurate, as disclosed, for example, in U.S. Application Publication No. 2011/0319559, each of which is incorporated by reference in its entirety. Other useful polyfunctionalizing agents include trimethylolpropane trivinyl ether, and the polythiols described in U.S. Pat. Nos. 4,366,307; 4,609,762; and 5,225,472. Mixtures of polyfunctionalizing agents may also be used. As a result, reactive antioxidants provided by the present disclosure may have a range of average functionality. For example, trifunctional thiols in combination with dithiols may afford average functionalities from 2.05 to 3.0, such as from 2.1 to 2.6. Wider ranges of average functionality may be achieved by using tetrafunctional and/or polyfunctionalizing agents having higher functionality. Functionality may also be determined by factors such as stoichiometry, as will be understood by those skilled in the art.

In reactive antioxidants of Formula (1d')-(1f') each $R^1$ can be $-((CH_2)_2-O-)_2-(CH_2)_2-$. For example, in reactive antioxidants of Formula (1d')-(1f'), each $R^1$ can be $-((CH_2)_2-O)_2-(CH_2)_2-$ such that reactive antioxidants have the structure of Formula (1h), Formula (1i), and Formula (1j), respectively:

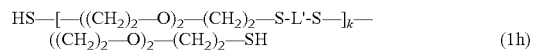  (1h)

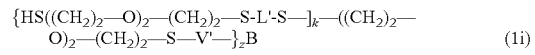  (1i)

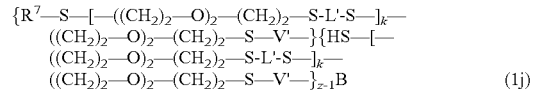  (1j)

where L', V', B, k, and z are defined as for Formula (1a)-(1c); and each $R^7$ is independently $\{-V'-\}\{HS-[-(CH_2)_2-O]_2-(CH_2)_2-S-L'-S-]_k-[(CH_2)_2-O]_2-(CH_2)_2-S-V'-\}_{z-1}B$.

In reactive antioxidants provided by the present disclosure, -L'- can be derived from the reaction of an antioxidant-containing precursor L comprising at least one antioxidant moiety and at least one group reactive with thiol groups. For example, L can comprise a single moiety that is reactive with two thiol groups, or L can comprise two or more reactive groups, each group reactive with a single thiol group. In antioxidants provided by the present disclosure, -L'- can comprise the structure —CH(—R⁴)— where R⁴ comprises an antioxidant moiety. The antioxidant moiety can be a moiety that is capable of thermally stabilizing a polymeric material such as, for example, a hindered phenol, a hindered aromatic amine, or a benzofuranone. An antioxidant-containing precursor can be a substituted benzaldehyde such as 3,5-di-tert-butyl-4-hydroxybenzaldehyde, 2,3,4-trihydroxybenzaldehyde, or a combination thereof. Reactive antioxidants provided by the present disclosure can be prepared using commercially available antioxidant-containing precursors or using commercially available antioxidant-containing precursors that have been modified to be reactive with two thiol groups.

In reactive antioxidants provided by the present disclosure, each $R^6$ can be hydrogen; each $R^3$ can be —(CH₂)₂—O—(CH₂)₂—O—(CH₂)₂—; each L' can be derived from a substituted benzaldehyde; each k can be 0, 1, or 2, wherein at least one k is not 0; B(—V)$_z$ can be triallyl cyanurate, wherein z is 3 and each —V is —O—CH₂—CH═CH₂; and $R^7$ can be {—V'—}{HS—[—(CH₂)₂—O—(CH₂)₂—O—(CH₂)₂—S-L'-S—]$_k$—(CH₂)₂—O—(CH₂)₂—O—(CH₂)₂—S—V'—}$_{z-1}$B.

In reactive antioxidants provided by the present disclosure, n in a moiety of Formula (2) can be an integer from 1 to 50, such as 1, 2, 3, or 4, an integer from 1 to 20, an integer from 1 to 10, or an integer from 1 to 3.

In moieties of Formula (2), each m can be independently an integer from 1 to 3. In moieties of Formula (1), each m can be the same and can be 1, 2, or 3.

In moieties of Formula (2), each $R^2$ can independently comprise a $C_{2-6}$ alkanediyl, such as ethanediyl, n-propanediyl, n-butanediyl, n-pentanediyl, or n-hexanediyl.

In moieties of Formula (2), m can be 1; and each $R^2$ can independently comprise a $C_{2-6}$ alkanediyl, such as ethanediyl, n-propanediyl, n-butanediyl, n-pentanediyl, or n-hexanediyl.

In moieties of Formula (2), m can be 2; and each $R^2$ can independently comprise a $C_{2-6}$ alkanediyl, such as ethanediyl, n-propanediyl, n-butanediyl, n-pentanediyl, or n-hexanediyl.

In reactive antioxidants provided by the present disclosure, n in Formula (2) can be at least 1, and $R^3$ can have the structure of Formula (2):

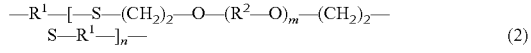

(2)

wherein, each $R^1$ is independently selected from $C_{2-10}$ alkanediyl, $C_{6-8}$ cycloalkanediyl, $C_{6-10}$ alkanecycloalkanediyl, a heterocyclic, —[(—CHR—)$_p$—X—]$_q$—(CHR)$_r$—, wherein each R is selected from hydrogen and methyl;

each $R^2$ is independently selected from $C_{2-10}$ n-alkanediyl, $C_{3-6}$ branched alkanediyl, $C_{6-8}$ cycloalkanediyl, $C_{6-14}$ alkanecycloalkanediyl, heterocyclic, and —[(—CH₂—)$_p$—X—]$_q$—(CH₂)$_r$—;

each X is independently selected from O, S, and —NR—, wherein R is selected from hydrogen and methyl;

m is an integer from 0 to 50;

n is an integer ranging from 1 to 60;

p is an integer ranging from 2 to 6;

q is an integer ranging from 1 to 5; and r is an integer ranging from 2 to 10.

In moieties of Formula (2), $R^1$ can be —[—(CHR)$_p$—X—]$_q$—(CHR)$_r$— wherein each X can be independently selected from —O— and —S—. In moieties of Formula (4), $R^1$ can be —[—(CHR)$_p$—X—]$_q$—(CHR)$_r$—, each X is —O— or each X is —S—.

In moieties of Formula (2), $R^1$ can be —[—(CH₂)$_p$—X—]$_q$—(CH₂)$_r$— wherein each X can be independently selected from —O— and —S—. In moieties of Formula (4), $R^1$ can be —[—(CH₂)$_p$—X—]$_q$—(CH₂)$_r$—, each X can be —O— or each X can be —S—.

In moieties of Formula (2), $R^1$ can be —[(—CH₂—)$_p$—X—]$_q$—(CH₂)$_r$—, where p is 2, X can be O, q can be 2, r can be 2, $R^2$ can be ethanediyl, m can be 2, and n can be 9.

In moieties of Formula (2), each $R^1$ can be derived from dimercaptodioxaoctane (DMDO) or each $R^1$ can be derived from dimercaptodiethylsulfide (DMDS).

In moieties of Formula (2), each p can be independently selected from 2, 3, 4, 5, and 6. In moieties of Formula (2), each p can be the same and can be 2, 3, 4, 5, or 6.

In moieties of Formula (2), each r can be selected from 2, 3, 4, 5, 6, 7, and 8.

In moieties of Formula (2), each q can be selected from 1, 2, 3, 4, and 5.

Moieties of Formula (2) are polythioethers and can be formed by reacting a dithiol with a divinyl ether. Suitable dithiols include those of Formula (3) and suitable divinyl ethers include divinyl ethers of Formula (5):

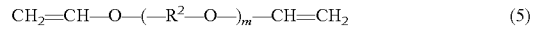

(5)

where m is 0 to 50 and $R^2$ in Formula (4) is selected from $C_{2-6}$ n-alkanediyl, $C_{3-6}$ branched alkanediyl, $C_{6-8}$ cycloalkanediyl, $C_{6-10}$ alkanecycloalkanediyl, and —[(CH₂—)$_p$O—]$_q$—(CH₂—)$_r$—, where p is an integer ranging from 2 to 6, q is an integer from 1 to 5, and r is an integer from 2 to 10. In in a divinyl ethers of Formula (5), $R^2$ can be $C_{2-6}$ n-alkanediyl, $C_{3-6}$ branched alkanediyl, $C_{6-8}$ cycloalkanediyl, $C_{6-10}$ alkanecycloalkanediyl, or —[(—CH₂—)$_p$—O—]$_q$—(—CH₂—)$_r$—.

Suitable divinyl ethers include, for example, compounds having at least one oxyalkanediyl group, such as from 1 to 4 oxyalkanediyl groups, i.e., compounds in which m in Formula (5) is an integer ranging from 1 to 4. M in Formula (5) can be an integer ranging from 2 to 4. It is also possible to employ commercially available divinyl ether mixtures that are characterized by a non-integral average value for the number of oxyalkanediyl units per molecule. Thus, m in Formula (5) can also be a rational number values ranging from 0 to 10.0, such as from 1.0 to 10.0, from 1.0 to 4.0, or from 2.0 to 4.0, such as 2.5, which represents an average functionality.

Examples of suitable vinyl ethers include, divinyl ether, ethylene glycol divinyl ether (EG-DVE) ($R^2$ in Formula (5) is ethanediyl and m is 1), butanediol divinyl ether (BD-DVE) ($R^2$ in Formula (5) is butanediyl and m is 1), hexanediol divinyl ether (HD-DVE) ($R^2$ in Formula (5) is hexanediyl and m is 1), diethylene glycol divinyl ether (DEG-DVE) ($R^2$ in Formula (5) is ethanediyl and m is 2), triethylene glycol divinyl ether ($R^2$ in Formula (5) is ethanediyl and m is 3), tetraethylene glycol divinyl ether ($R^2$ in Formula (5) is ethanediyl and m is 4), cyclohexanedimethanol divinyl ether, polytetrahydrofuryl divinyl ether; trivinyl ether monomers, such as trimethylolpropane trivinyl ether; tetrafunctional ether monomers, such as pentaerythritol tetravinyl ether; and combinations of two or more such polyvinyl ether monomers. A polyvinyl ether may have one or more pendant groups selected from alkyl groups, hydroxy groups, alkoxy groups, and amine groups.

Divinyl ethers in which $R^2$ in Formula (5) is $C_{3-6}$ branched alkanediyl may be prepared by reacting a polyhydroxy compound with acetylene. Examples of branched divinyl ethers include compounds in which $R^2$ in Formula (5) is an alkyl-substituted methanediyl group such as —CH(—CH$_3$)—, for which $R^2$ in Formula (5) is ethanediyl and m is 3 or an alkyl-substituted ethanediyl.

Other useful divinyl ethers include compounds in which $R^2$ in Formula (5) is polytetrahydrofuryl (poly-THF) or polyoxyalkanediyl, such as those having an average of about 3 monomer units.

Reactive antioxidants and/or antioxidant-containing prepolymers provided by the present disclosure may have a molecular weight less than 5,000 Daltons, less than 4,000 Daltons, less than 3,000 Daltons, less than 2,000 Daltons, or less than 1,000 Daltons. Reactive antioxidants provided by the present disclosure may have a molecular weight from 300 Daltons to 5,000 Daltons, from 300 Daltons, to 4,000 Daltons, from 300 Daltons, to 3,000 Daltons, from 300 Daltons to 2,000 Daltons, or from 300 Daltons to 1,000 Daltons. Reactive antioxidants provided by the present disclosure may have a mercaptan equivalent weight from 200 to 800, from 200 to 700, from 200 to 600, from 200 to 500, or from 200 to 400.

Reactive antioxidants provided by the present disclosure may be difunctional, trifunctional, or have a functionality of 4, 5, 6, or a functionality greater than 6. Reactive antioxidants also include mixtures of reactive antioxidants having different functionalities. Mixtures of reactive antioxidants can be characterized by an average non-integer functionality. For example, a reactive antioxidant can include a mixture of difunctional, trifunctional, and tetrafunctional reactive antioxidants characterized by an average non-integer functionality from 2.1 to 3.9, such as, for example, 2-8.

Reactive antioxidants provided by the present disclosure may comprise one antioxidant moiety, two antioxidant moieties, three antioxidant moieties, or more than three antioxidant moieties. Reactive antioxidants provided by the present disclosure may comprise from 1 to 10 antioxidant moieties, from 1 to 8 antioxidant moieties, from 1 to 6 antioxidant moieties, or from 1 to 3 antioxidant moieties.

Reactive antioxidants provided by the present disclosure, such as those in which n is 2 to 60, may have a molecular weight greater than 5,000 Daltons. Reactive antioxidants having a molecular weight greater than 5,000 Daltons can be referred to as antioxidant-containing prepolymers. It is not intended that there be a clear distinction between reactive antioxidants and antioxidant-containing prepolymers other than that the former generally have a lower molecular weight and the latter generally have a higher molecular weight. Compositions provided by the present disclosure may comprise a mixture of low molecular weight and high molecular weight reactive antioxidants and/or antioxidant-containing prepolymers

Methods of Preparing Reactive Antioxidants

Reactive antioxidants provided by the present disclosure may comprise the reaction product of reactants comprising (a) a dithiol, and (b) an antioxidant-containing precursor comprising at least one antioxidant moiety and at least one moiety reactive with thiol groups. Polyfunctional reactive antioxidants provided by the present disclosure may comprise the reaction product of reactants comprising (a) a dithiol, (b) an antioxidant-containing precursor comprising at least one antioxidant moiety and at least one moiety reactive with thiol groups; and (c) a polyfunctionalizing agent comprising terminal thiol groups. Polyfunctional reactive antioxidants provided by the present disclosure may also comprise the reaction products of (a) a reactive antioxidant provided by a present disclosure, and (b) a polyfunctionalizing agent comprising terminal groups reactive with the reactive antioxidant.

A dithiol can have the structure of Formula (3):

$$HS-R^1-SH \qquad (3)$$

where, each $R^1$ independently is selected from $C_{2-10}$ alkanediyl, $C_{6-8}$ cycloalkanediyl, $C_{6-10}$ alkanecycloalkanediyl, $C_{5-8}$ heterocycloalkanediyl, and —[(—CHR—)$_p$—X—]$_q$—(—CHR—)$_r$—, wherein:

p is an integer from 2 to 6;
q is an integer from 1 to 5;
r is an integer from 2 to 10;
each R is independently selected from hydrogen and methyl; and
each X is independently selected from —O—, —S—, and —NR$^5$—, wherein R$^5$ is selected from hydrogen and methyl.

In a dithiol of Formula (3), $R^1$ can be —[—(CHR)$_p$—X—]$_q$—(CHR)$_r$—.

In a dithiol of Formula (3), X can be selected from —O— and —S—, and thus —[—(CHR)$_p$—X—]$_q$—(CHR)$_r$— in Formula (3) can be —[(—CHR—)$_p$—O—]$_q$—(CHR)$_r$— or —[(—CHR—)$_p$—S—]$_q$—(CHR)$_r$—. P and r can be equal, such as where p and r can be both two, both 3 or both 4.

In a dithiol of Formula (3), $R^1$ can be selected from $C_{2-6}$ alkanediyl and —[—(CHR)$_p$—X—]$_q$—(CHR)$_r$—.

In a dithiol of Formula (3), $R^1$ can be —[—(CHR)$_p$—X—]$_q$—(CHR)$_r$—, wherein X can be —O—, or X can be —S—.

In a dithiol of Formula (3), $R^1$ can be —[—(CHR)$_p$—X—]$_q$(CHR)$_r$—, p can be 2, r can be 2, q can be 1, and X can be —S—; or p can be 2, q can be 2, r can be 2, and X can be —O—; or p can be 2, r can be 2, q can be 1, and X can be —O—.

In a dithiol of Formula (3), $R^1$ can be —[—(CHR)$_p$—X—]$_q$—(CHR)$_r$—, each R can be hydrogen, at least one R can be methyl and each of the other R can be hydrogen.

In a dithiol of Formula (3), each 12' can be derived from dimercaptodioxaoctane (DMDO) or each $R^1$ can be derived from dimercaptodiethylsulfide (DMDS).

In a dithiol of Formula (3) each can be independently an integer from 1 to 3, or each m can be the same and can be 1, 2, or 3.

In a dithiol of Formula (3), n can be an integer from 1 to 30, an integer from 1 to 20, an integer from 1 to 10, or an integer from 1 to 5. In addition, n may be any integer from 1 to 60.

In a dithiol of Formula (3), each p can be independently selected from 2, 3, 4, 5, and 6; or each p can be the same and can be 2, 3, 4, 5, or 6.

In a dithiol of Formula (3), each r can be selected from 2, 3, 4, 5, 6, 7, and 8.

In a dithiol of Formula (3), each q can be selected from 1, 2, 3, 4, and 5

Examples of suitable dithiols of Formula (3) include 1,2-ethanedithiol, 1,2-propanedithiol, 1,3-propanedithiol, 1,3-butanedithiol, 1,4-butanedithiol, 2,3-butanedithiol, 1,3-pentanedithiol, 1,5-pentanedithiol, 1,6-hexanedithiol, 1,3-dimercapto-3-methylbutane, dipentenedimercaptan, ethylcyclohexyldithiol (ECHDT), dimercaptodiethylsulfide, methyl-substituted dimercaptodiethylsulfide, dimethyl-substituted dimercaptodiethylsulfide, dimercaptodioxaoctane, 1,5-dimercapto-3-oxapentane, and a combination of any of the foregoing. A dithiol may have one or more pendant groups selected from a lower (e.g., $C_{1-6}$) alkyl group, a lower alkoxy group, and a hydroxyl group. Suitable alkyl pendant groups include, for example, $C_{1-6}$ linear alkyl, $C_{3-6}$ branched alkyl, cyclopentyl, and cyclohexyl.

Other examples of suitable dithiols include dimercaptodiethylsulfide (DMDS) (in Formula (3), $R^1$ is $—[(CH_2—)_p—X-]_q—(CH_2)_r—$, where p is 2, r is 2, q is 1, and X is —S—); dimercaptodioxaoctane (DMDO) (in Formula (3), $R^1$ is $—[(CH_2—)_p—X—]_q—(CH_2)_r—$, wherein p is 2, q is 2, r is 2, and X is —O—); and 1,5-dimercapto-3-oxapentane (in Formula (3), $R^1$ is $—[(CH_2—)_p—X—]_q—(CH_2)_r—$, wherein p is 2, r is 2, q is 1, and X is —O—). It is also possible to use dithiols that include both heteroatoms in the carbon backbone and pendant alkyl groups, such as methyl groups. Such dithiols include, for example, methyl-substituted DMDS, such as HS—$CH_2CH(CH_3)$—S—$CH_2CH_2$—SH, HS—$CH(CH_3)CH_2$—S—$CH_2CH_2$—SH and dimethyl substituted DMDS, such as HS—$CH_2CH(CH_3)$—S—$CHCH_3CH_2$—SH and HS—$CH(CH_3)CH_2$—S—$CH_2CH(CH_3)$—SH.

Polyfunctionalizing agents suitable for use in preparing polyfunctional reactive antioxidants and antioxidant-containing prepolymers include trifunctionalizing agents, that is, compounds where z is 3. Suitable trifunctionalizing agents include, for example, triallyl cyanurate (TAC), 1,2,3-propanetrithiol, isocyanurate-containing trithiols, and combinations thereof, as disclosed, for example, in U.S. Application Publication No. 2010/0010133, which is incorporated by reference in its entirety, and isocyanurates as disclosed, for example, in U.S. Application Publication No. 2011/0319559, which is incorporated by reference in its entirety. Other useful polyfunctionalizing agents include trimethylolpropane trivinyl ether, and the polythiols described in U.S. Pat. Nos. 4,366,307; 4,609,762; and 5,225,472, each of which is incorporated by reference in its entirety. Mixtures of polyfunctionalizing agents may also be used. As a result, polythioethers provided by the present disclosure may have a wide range of average functionality. For example, trifunctionalizing agents may afford average functionalities from 2.05 to 3.0, such as from 2.1 to 2.6. Wider ranges of average functionality may be achieved by using tetrafunctional or higher functionality polyfunctionalizing agents. Functionality may also be determined by factors such as stoichiometry, as will be understood by those skilled in the art. A thiol-terminated precursor can be prepared by reacting an alkenyl-terminated polyfunctionalizing agent such as TAC with a dithiol, such as a dithiol of Formula (3), for example, DMDO, to provide a thiol-terminated polyfunctionalizing agent. The thiol-terminated polyfunctionalizing agent may then be reacted with an antioxidant having groups reactive with thiol groups, and a dithiol and/or a polythiol.

Reactive antioxidants provided by the present disclosure may be prepared by reacting one or more polythiols with one or more antioxidant-containing precursors comprising at least one group reactive with thiol groups and at least one antioxidant moiety. For example, a reactive antioxidant may be prepared by reacting one or more polythiols of Formula (3) with one or more antioxidant-containing precursors such as a substituted benzaldehyde in the presence of a catalyst such as a solid acid catalyst. The reactants may be reacted in a suitable ratio to provide reactive antioxidants having a functionality, for example, from 2 to 6, such as from 2.1 to 2.9, or from 2.1 to 2.3, and comprising one or more antioxidant moieties Reactive antioxidants provided by the present disclosure can be added to a sealant composition. During curing of the sealant composition, the terminal reactive groups of the reactive antioxidant can react with a prepolymer or a curing agent such that the reactive antioxidant becomes covalently bound to the cured polymer network. The reactive antioxidant can also function as the base or prepolymer component of a sealant composition, which can optionally include a lower molecular weight reactive antioxidant.

A reactive antioxidant and/or antioxidant-containing prepolymer can comprise terminal groups reactive with the curing agent. The terminal groups of the reactive antioxidant may be the same as the terminal groups of an antioxidant-containing prepolymer or other prepolymer in the composition. For example, the reactive antioxidant and the prepolymer may comprise terminal thiol groups that are reactive with the curing agent, such as a polyepoxide curing agent.

A reactive antioxidant may comprise terminal groups reactive with a prepolymer. The terminal reactive groups of the reactive antioxidant may comprise the same terminal groups as the curing agent or may function as the curing agent in the composition. For example, a reactive antioxidant and a curing agent may comprise terminal epoxy groups, alkenyl groups, Michael acceptor groups, thiol groups, amine groups, hydroxyl groups, polyalkoxysilyl groups, or isocyanate groups as suitable for a particular curing chemistry.

Antioxidant-containing Sulfur-Containing Prepolymers

Reactive antioxidants provided by the present disclosure may also serve as precursors for antioxidant-containing prepolymers in which an antioxidant is incorporated into the backbone of a prepolymer. For example, antioxidant-containing polythioether prepolymers provided by the present disclosure may be prepared by reacting a dithiol of Formula (3) and optionally a polyfunctionalizing agent, a thiol-terminated reactive antioxidant, and a divinyl ether; or may be prepared by reacting a thiol-terminated antioxidant with a divinyl ether. For example, an antioxidant-containing polythioether provided by the present disclosure may be prepared by reacting a thiol-terminated reactive antioxidant of Formula (1a')-(1c'), a dithiol of Formula (3), and a divinyl ether of Formula (5).

Two or more types of reactive antioxidants, dithiols of Formula (3), and/or polyvinyl ether monomers of Formula (5) may be used to prepare a thiol-terminated antioxidant-containing polythioether provided by the present disclosure. The reactants may further include a polyfunctionalizing agent which may include a polyfunctional reactive antioxidant, a polythiol, and/or a polyalkenyl compound.

A polyvinyl ether monomer may comprise 20 mole percent to less than 50 mole percent of the reactants used to prepare a thiol-terminated polythioether prepolymer, or from 30 mole percent to less than 50 mole percent.

Relative amounts of dithiols and divinyl ethers can be selected to yield oxidant-containing polythioethers having terminal thiol groups. For example, a thiol-terminated reactive antioxidant and/or dithiol of Formula (3) or a mixture of at least two different thiol-terminated reactive antioxidants and/or dithiols of Formula (3), can be reacted with of a divinyl ether of Formula (5) or a mixture of at least two different divinyl ethers of Formula (5) in relative amounts such that the molar ratio of thiol groups to alkenyl groups is greater than 1:1, such as from 1.1:1.0 to 2.0:1.0.

The reaction between thiol-terminated reactive antioxidants, dithiols and divinyl ethers and/or polythiols and polyvinyl ethers may be catalyzed by a free radical catalyst. Suitable free radical catalysts include, for example, azo compounds, for example azobisnitriles such as azo(bis)isobutyronitrile (AIBN); organic peroxides such as benzoyl peroxide and t-butyl peroxide; and inorganic peroxides such as hydrogen peroxide. The catalyst may be a free-radical catalyst, an ionic catalyst, or ultraviolet radiation. A catalyst may not comprise acidic or basic compounds, and does not produce acidic or basic compounds upon decomposition. Examples of suitable free-radical catalysts include azo-type catalyst, such as Vazo®-57 (Du Pont), Vazo®-64 (Du Pont), Vazo®-67 (Du Pont), V-70® (Wako Specialty Chemicals), and V-65B® (Wako Specialty Chemicals). Examples of other suitable free-radical catalysts include alkyl peroxides, such as tert-butyl peroxide. The reaction may also be effected by irradiation with ultraviolet light either with or without a cationic photoinitiating moiety.

As another example, antioxidant-containing polythioethers provided by the present disclosure may be prepared by reacting a reactive antioxidant of Formula (1a'), Formula (1b'), Formula (1c') or a combination thereof, with a divinyl ether, such as a divinyl ether of Formula (5). An antioxidant may be incorporated into the backbone of antioxidant-containing polythioethers by reacting a thiol-terminated polythioether with an antioxidant-containing precursor comprising at least one antioxidant moiety and at least one moiety reactive with thiol groups.

Similar methods are applicable to other thiol-terminated sulfur-containing prepolymers. A sulfur-containing prepolymer can be thiol-terminated, accordingly, a sulfur-containing prepolymer may include thiol-terminated polythioether prepolymers, a thiol-terminated polysulfide prepolymers, a thiol-terminated sulfur-containing polyformal prepolymers, or a combination of any of the foregoing.

Sulfur-containing prepolymers provided by the present disclosure may be selected from a polythioether, a polysulfide, a sulfur-containing polyformal, and a combination of any of the foregoing. A sulfur-containing prepolymer may comprise a polythioether or a sulfur-containing prepolymer may comprise a polysulfide. A sulfur-containing prepolymer may comprise a mixture of different polythioethers and/or polysulfides, and the polythioethers and/or polysulfides may have the same or different functionality. A sulfur-containing prepolymer can have an average functionality from 2 to 6, from 2 to 4, from 2 to 3, from 2.3 to 2.8, or from 2.05 to 2.5. For example, a sulfur-containing prepolymer can comprise a difunctional sulfur-containing prepolymer, a trifunctional sulfur-containing prepolymer, and a combination thereof. A sulfur-containing prepolymer can comprise a sulfur-containing polyformal.

To incorporate an antioxidant into a backbone of a sulfur-containing prepolymer, an antioxidant-containing precursor comprising at least one group reactive with thiol groups can be reacted with a thiol-terminated sulfur-containing prepolymer.

Methods of Synthesizing Thiol-Terminated Antioxidant-Containing Prepolymers

A thiol-terminated antioxidant-containing polythioether prepolymer such as a thiol-terminated antioxidant-containing polythioether prepolymer may be prepared by reacting a difunctional thiol-terminated polythioether prepolymer or a mixture of difunctional thiol-terminated polythioether prepolymers with an antioxidant-containing precursor having at least one antioxidant moiety and at least one group reactive with thiol groups.

For example, methods of preparing a thiol-terminated antioxidant-containing polythioether prepolymer of Formula (6a), may comprise reacting (N+1) moles of a thiol-terminated polythioether prepolymer of Formula (7a) with (N) moles of an antioxidant-containing precursor L:

H-A-[-L'-A-]$_N$-H (6a)

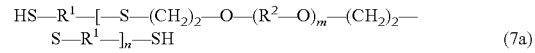

HS—R$^1$—[—S—(CH$_2$)$_2$—O—(R$^2$—O)$_m$—(CH$_2$)$_2$—S—R$^1$—]$_n$—SH (7a)

wherein:

N is an integer from 1 to 10;

each L' is derived from the reaction of an antioxidant L with thiol groups;

each A is independently a moiety of Formula (8):

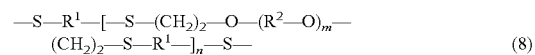

—S—R$^1$—[—S—(CH$_2$)$_2$—O—(R$^2$—O)$_m$—(CH$_2$)$_2$—S—R$^1$—]$_n$—S— (8)

wherein, each $R^1$ independently comprises $C_{2-10}$ alkanediyl, $C_{6-8}$ cycloalkanediyl, $C_{6-10}$ alkanecycloalkanediyl, $C_{5-8}$ heterocycloalkanediyl, or —[(—CHR—)$_p$—X—]$_q$—(—CHR—)$_r$—, wherein:

p is an integer from 2 to 6;

q is an integer from 1 to 5;

r is an integer from 2 to 10;

each R independently comprises hydrogen or methyl; and each X independently comprises —O—, —S—, or —NR—, wherein R comprises hydrogen or methyl; and each $R^2$ independently comprises $C_{1-10}$ alkanediyl, $C_{6-8}$ cycloalkanediyl, $C_{6-14}$ alkanecycloalkanediyl, or —[(—CHR—)$_p$—X—]$_q$—(—CHR—)$_r$—, wherein p, q, r, R, and X are as defined for $R^1$;

m is an integer from 0 to 50; and n is an integer from 1 to 60.

In a thiol-terminated antioxidant-containing sulfur-containing prepolymer of Formula (6a), N can be 1, 2, 3, 4, 5, 6, 7, 8, 9 or 10. In a thiol-terminated antioxidant-containing polythioether prepolymer of Formula (6a), the molecular weight can be, for example, from 200 Daltons to 20,000 Daltons or from 1000 Daltons to 10,000 Daltons. Thiol-terminated antioxidant-containing polythioether prepolymers can comprise a combination of antioxidant-containing polythioether prepolymers of Formula (6a) with different values for N. In thiol-terminated antioxidant-containing prepolymers of Formula (6a), N can be 1. Thus, in practice, when preparing a thiol-terminated antioxidant-containing polythioether prepolymer of Formula (6a), the molar ratio of thiol-terminated polythioether prepolymer to antioxidant need not be a whole number such that thiol-terminated antioxidant-containing prepolymers of Formula (6a) represent a mixture of thiol-terminated antioxidant-containing polythioether prepolymers having different values of N.

Methods of preparing a thiol-terminated antioxidant-containing polythioether prepolymer of Formula (6b) can comprise reacting (z) moles of a thiol-terminated antioxidant-containing polythioether prepolymer of Formula (6a) with one (1) mole of a polyfunctionalizing agent B {V}$_z$:

{H-A-[-L'-A-]$_N$-V—}$_z$B (6b)

H-A-[-L'-A-]$_N$-H (6a)

wherein,

N is an integer from 1 to 10;

each L' comprises an antioxidant moiety derived from the reaction of antioxidant-containing precursor L with thiol groups;

each A is independently a moiety of Formula (8):

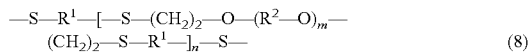

$$-S-R^1-[-S-(CH_2)_2-O-(R^2-O)_m-(CH_2)_2-S-R^1-]_n-S- \quad (8)$$

wherein:

each $R^1$ independently comprises $C_{2-10}$ alkanediyl, $C_{6-8}$ cycloalkanediyl, $C_{6-10}$ alkanecycloalkanediyl, $C_{5-8}$ heterocycloalkanediyl, or $-[(-CHR-)_p-X-]_q-(-CHR-)_r-$, wherein:

p is an integer from 2 to 6;

q is an integer from 1 to 5;

r is an integer from 2 to 10;

each R independently comprises hydrogen or methyl; and each X independently comprises $-O-$, $-S-$, or $-NR-$, wherein R comprises hydrogen or methyl;

each $R^2$ independently comprises $C_{1-10}$ alkanediyl, $C_{6-8}$ cycloalkanediyl, $C_{6-14}$ alkanecycloalkanediyl, or $-[(-CHR-)_p-X-]_q-(-CHR-)_r-$, wherein p, q, r, R, and X are as defined for $R^1$;

m is an integer from 0 to 50; and n is an integer from 1 to 60; and

B represents a core of a z-valent polyfunctionalizing agent $B(-V)_z$ wherein:

z is an integer from 3 to 6;

each V is a group comprising a terminal group reactive with a terminal thiol group; and each $-V'-$ is derived from the reaction of $-V$ with a thiol.

A reactive antioxidant can be prepared from a polythiol comprising a thiol-terminated polythioether of Formula (7a), a thiol-terminated polythioether of Formula (7b), or a combination thereof:

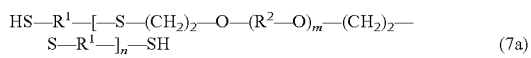

$$HS-R^1-[-S-(CH_2)_2-O-(R^2-O)_m-(CH_2)_2-S-R^1-]_n-SH \quad (7a)$$

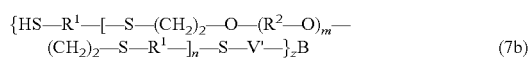

$$\{HS-R^1-[-S-(CH_2)_2-O-(R^2-O)_m-(CH_2)_2-S-R^1-]_n-S-V'-\}_zB \quad (7b)$$

wherein:

each $R^1$ independently comprises $C_{2-10}$ alkanediyl, $C_{6-8}$ cycloalkanediyl, $C_{6-10}$ alkanecycloalkanediyl, $C_{5-8}$ heterocycloalkanediyl, or $-[(-CHR-)_p-X-]_q-(-CHR-)_r-$, wherein:

p is an integer from 2 to 6;

q is an integer from 1 to 5;

r is an integer from 2 to 10;

each R independently comprises hydrogen or methyl; and each X independently comprises $-O-$, $-S-$, or $-NR-$, wherein R is selected from hydrogen and methyl;

each $R^2$ independently comprises $C_{1-10}$ alkanediyl, $C_{6-8}$ cycloalkanediyl, $C_{6-14}$ alkanecycloalkanediyl, or $-[(-CHR-)_p-X-]_q-(-CHR-)_r-$, wherein p, q, r, R, and X are as defined for $R^1$;

m is an integer from 0 to 50;

n is an integer from 1 to 60;

B represents a core of a z-valent polyfunctionalizing agent $B(-V)_z$ wherein:

z is an integer from 3 to 6;

each V is a moiety comprising a terminal group reactive with terminal thiol groups; and each $-V'-$ is derived from the reaction of $-V$ with a thiol.

A reaction between a thiol-terminated antioxidant-containing polythioether prepolymer and an antioxidant can be performed in the presence of a catalyst such as an amine catalyst including, for example, any of the amine catalysts disclosed herein.

Terminal-Modified Antioxidant-Containing, Sulfur-Containing Prepolymers

Reactive antioxidants and antioxidant-containing polythioether prepolymers may be adapted for use with a particular curing chemistry by capping or terminating a reactive antioxidant or an antioxidant-containing polythioether prepolymer such as a thiol-terminated antioxidant-containing polythioether prepolymer with a suitable functional group. Capped analogs of thiol-terminated polythioethers are disclosed, for example, in U.S. Pat. No. 6,172,179 and in U.S. Application Publication No. 2011/0319559. For example, a reactive antioxidant or an antioxidant-containing polythioether prepolymer can have terminal groups other than unreacted thiol groups, such as hydroxyl, alkenyl, isocyanate, amine, a hydrolysable functional group such as a polyalkoxysilyl group, a Michael acceptor group, or an epoxy group.

Antioxidant-containing, sulfur-containing prepolymers provided by the present disclosure can include terminal-modified antioxidant-containing sulfur-containing prepolymers. Terminal-modified antioxidant-containing prepolymers can also be referred to as capped prepolymers. Terminal-modified antioxidant-containing sulfur-containing prepolymers can be prepared by reacting a thiol-terminated antioxidant-containing sulfur-containing prepolymer with a compound having a reactive terminal group and a group reactive with a thiol group.

The preparation of terminal-modified sulfur-containing polythioethers is known in the art. For example, isocyanate-terminated polythioethers are disclosed in U.S. application Ser. No. 14/200,687 filed on Mar. 7, 2014, polyalkoxysilyl-terminated polythioethers are disclosed in U.S. application Ser. No. 14/200,687 filed on Mar. 7, 2014, alkenyl-terminated polythioethers are disclosed in U.S. Application Publication No. 2006/0270796; and epoxy-terminated polythioethers are disclosed in U.S. Application Publication No. 2005/0010003, each of which is incorporated by reference in its entirety.

Capped analogs may be prepared by a number of methods known to those skilled in the art. For example, to obtain capped antioxidant-containing polythioethers antioxidant prepolymers, a thiol-terminated antioxidant-containing polythioether prepolymer may be reacted with a compound having a terminal group reactive with thiol groups.

To obtain an alkenyl-terminated reactive antioxidant or antioxidant-containing polythioether prepolymer, a thiol-terminated reactive antioxidant or a thiol-terminated antioxidant-containing polythioether prepolymer may be reacted with a compound containing a terminal alkenyl group and an isocyanate group such as a group derived from TMI, 2-isocyanatoethyl methacrylate, or allyl isocyanate, in the presence of dibutyltin dilaurate catalyst.

Polyalkoxysilyl-terminated reactive antioxidants or antioxidant-containing polythioether prepolymers may be prepared, for example, by reacting a thiol-terminated reactive antioxidant or a thiol-terminated antioxidant-containing polythioether prepolymer with an isocyanatoalkyltrialkoxysilane such as a 3-isocyanatopropyltrimethoxysilane or 3-isocyanatopropyltriethoxysilane in the presence of dibutyltin dilaurate to provide the corresponding polyalkoxysilyl-terminated antioxidant-containing polythioether prepolymer. A polyalkoxysilyl-terminated reactive antioxidant or antioxidant-containing polythioether may also be prepared by reacting a vinyl alkoxysilane with a thiol-terminated antioxidant-containing polythioether.

Epoxy-terminated reactive antioxidants and antioxidant-containing polythioether prepolymers may be prepared, for example, by reacting a thiol-terminated reactive antioxidant or thiol-terminated antioxidant-containing polythioether prepolymer in the presence of a monoepoxide such as allyl glycidyl ether to provide the corresponding epoxy-terminated reactive antioxidant or antioxidant-containing polythioether prepolymer.

Amine-terminated reactive antioxidants or antioxidant-containing prepolymers may be prepared, for example, by reacting a thiol-terminated reactive antioxidant or antioxidant-containing polythioether prepolymer with a monofunctional 4-amino butyl vinyl ether with a free-radical initiator. Alternatively, an amine-terminated reactive antioxidant or antioxidant-containing polythioether prepolymer may be obtained by reacting an isocyanate-terminated reactive antioxidant or antioxidant-containing polythioether prepolymer with a diamine such as 4-(aminomethyl)aniline to provide the corresponding amine-terminated reactive antioxidant or antioxidant-containing polythioether prepolymer. Amine-terminated reactive antioxidants or antioxidant-containing polythioethers prepolymers may also be obtained by reacting a thiol-terminated reactive antioxidant or antioxidant-containing polythioether or an alkanol-terminated or hydroxy-terminated reactive antioxidant or antioxidant-containing prepolymer with an amino-substituted benzoate such as ethyl-4-aminobenzoate in the presence of $Bu_2SnO$ or NaOMe at elevated temperature to provide the corresponding amine-terminated reactive antioxidant or antioxidant-containing polythioether.

For example, amine-terminated reactive antioxidants or antioxidant-containing polythioethers may be prepared, for example, by reacting an activated alkenyl-terminated reactive antioxidant or antioxidant-containing polythioether or a Michael acceptor-terminated reactive antioxidant or antioxidant-containing polythioether with a diamine, an amino-substituted aniline such as 4-(aminomethyl)aniline, or an alkylamine such as n-butylamine, optionally in the presence of a catalyst such as 1,8-diazabicyclo[5.4.0]undec-7-ene (DBU) in an organic solvent to provide the corresponding amine-terminated reactive antioxidant or antioxidant-containing polythioether. Alternatively, amine-terminated reactive antioxidant or antioxidant-containing polythioethers may be obtained by reacting an isocyanate-terminated reactive antioxidant or antioxidant-containing polythioether with a diamine such as 4-(aminomethyl)aniline to provide the corresponding amine-terminated reactive antioxidant or antioxidant-containing polythioether Amine-terminated reactive antioxidants or antioxidant-containing polythioethers may also be obtained by reacting a hydroxyl-terminated reactive antioxidant or antioxidant-containing polythioether with an amino-substituted benzoate such as ethyl-4-aminobenzoate in the presence of $Bu_2SnO$ or NaOMe at elevated temperature to provide the corresponding amine-terminated reactive antioxidant or antioxidant-containing polythioether.

Isocyanate-terminated reactive antioxidants or antioxidant-containing polythioethers prepolymers may be prepared, for example, by reacting a thiol-terminated reactive antioxidant or antioxidant-containing polythioether prepolymer with a diisocyanate such as TDI, Isonate™ 143L (polycarbodiimide-modified diphenylmethane diisocyanate), Desmodur® N3400 (1,3-diazetidine-2,4-dione, 1,3-bis(6-isocyanatohexyl)-), IPDI (isophorone diisocyanate), or Desmodur® W ($H_{12}$MDI) optionally in the presence of a catalyst such as dibutyltin dilaurate. Isocyanate-terminated reactive antioxidants or antioxidant-containing polythioethers prepolymers may be used as intermediates in the synthesis of other terminal-modified reactive antioxidant or antioxidant-containing polythioether prepolymers such as certain amine-terminated and thiol-terminated reactive antioxidants or antioxidant-containing polythioether prepolymers.

Hydroxyl-terminated reactive antioxidants or antioxidant-containing polythioethers prepolymers may be prepared, for example, by reacting a thiol-terminated reactive antioxidant or antioxidant-containing polythioether prepolymer with a compound having a terminal hydroxyl group and a group reactive with thiol groups.

Reactive antioxidant or antioxidant-containing polythioether prepolymers may be terminated with Michael acceptor groups. A Michael acceptor group can be derived from a vinyl sulfone and has the structure of Formula (9):

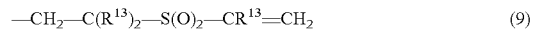

wherein each $R^{13}$ can be independently selected from hydrogen and $C_{1-3}$ alkyl. In moieties of Formula (9), each $R^{13}$ can be hydrogen. Michael acceptor-terminated antioxidant-containing polythioethers may be prepared, for example, by reacting a thiol-terminated reactive antioxidant or antioxidant-containing polythioether with a compound having a terminal Michael acceptor group and a group reactive with thiol groups such as a divinylsulfone, in the presence of an amine catalyst. Michael acceptor/polythioether chemistries and compounds are disclosed in U.S. Application Publication No. 2013/0345371, which is incorporated by reference in its entirety. Examples of isocyanate- and epoxy-capped polythioethers and methods of making isocyanate- and epoxy-capped polythioethers are disclosed, for example, in U.S. Pat. No. 7,879,955 B2.

Compositions

Cured compositions such as coatings or sealants provided by the present disclosure include antioxidants covalently bound to the cured polymer network.

Uncured compositions provided by the present disclosure can include a reactive antioxidant, an antioxidant-containing, sulfur-containing prepolymer, or a combination thereof.

Uncured compositions provided by the present disclosure may also include one or more additional sulfur-containing prepolymers, a curing agent, or a combination thereof.

In uncured compositions provided by the present disclosure the reactive antioxidant, antioxidant-containing sulfur-containing prepolymer, and/or additional sulfur-containing prepolymer may be terminated with the same reactive group, and the curing agent may be reactive with reactive terminal groups.

In uncured compositions provided by the present disclosure the reactive antioxidant, antioxidant-containing sulfur-containing prepolymer, and/or additional sulfur-containing prepolymer may be thiol terminated and the curing agent may be reactive with thiol groups.

Uncured compositions provided by the present disclosure can contain a thiol-terminated reactive antioxidant and a thiol-terminated polythioether, where the thiol-terminated polythioether may include a thiol-terminated antioxidant-containing polythioether.

Compositions provided by the present disclosure may comprise one or more reactive antioxidants and one or more sulfur-containing prepolymers, and no antioxidant-containing prepolymers.

Compositions provided by the present disclosure may contain from 0.05 wt % to 10 wt %, from 0.1 wt % to 6 wt % from 0.5 wt % to 4 wt %, or from 0.5 wt % to 2 wt % of an antioxidant moiety, wherein wt % is based on the total solids weight of a composition.

The amount of reactive antioxidant in a composition can be selected to provide enhanced stability of the cured composition upon exposure of the cured composition to aviation fuel and environmental stress.

Curable compositions provided by the present disclosure may further include a curing agent. Compositions may further include additives, catalysts, fillers, and/or other sulfur-containing prepolymers including for example, polythioethers, sulfur-containing polyformals, and/or polysulfides.

Curing Agents

Compositions provided by the present disclosure may comprise a curing agent comprising two or more reactive groups that are reactive with the terminal reactive groups of the reactive antioxidant, the antioxidant-containing prepolymer, and/or additional sulfur-containing prepolymer. In compositions comprising a thiol-terminated reactive antioxidant, a thiol-terminated antioxidant-containing prepolymer, and/or an additional thiol-terminated prepolymer, the curing agent can be a polyepoxy curing agent.

Uncapped and capped reactive antioxidant or antioxidant-containing sulfur-containing prepolymers, including uncapped and capped reactive antioxidants and antioxidant-containing polythioether prepolymers provided by the present disclosure can be liquid at room temperature. Uncapped and capped reactive antioxidants and antioxidant-containing sulfur-containing prepolymers including uncapped and capped antioxidant-containing polythioether prepolymers provided by the present disclosure can have a viscosity, at 100% solids, of less than 500 poise, such as 100 poise to 300 poise or, in some cases, 100 poise to 200 poise at a temperature of about 25° C. and a pressure of about 760 mm Hg, determined according to ASTM D-2849 §79-90 and measured using a Brookfield CAP 2000 viscometer. Any endpoint within the foregoing ranges can also be used. Uncapped and capped reactive antioxidant or antioxidant-containing sulfur-containing prepolymers including uncapped and capped antioxidant-containing polythioether prepolymers provided by the present disclosure can have a number average molecular weight of 400 grams per mole to 10,000 grams per mole, such as 1,000 grams per mole to 8,000 grams per mole, the molecular weight being determined, for example, by gel permeation chromatography using a polystyrene standard. Any endpoints within the foregoing ranges can also be used. The $T_g$ uncapped and capped reactive antioxidants or antioxidant-containing sulfur-containing prepolymers including uncapped and capped antioxidant-containing polythioether prepolymers provided by the present disclosure is not higher than −55° C., such as not higher than −60° C.

Curing agents useful in compositions provided by the present disclosure include compounds that are reactive with the terminal groups of the reactive antioxidant and/or antioxidant-containing prepolymer, such as compounds that are reactive with hydroxyl groups, alkenyl groups, epoxy groups, thiol groups, amine groups, isocyanate groups, or Michael acceptor groups.

In compositions containing a reactive antioxidant and/or antioxidant-containing prepolymer terminated with thiol groups, a suitable curing agent can be a polyepoxide. Examples of suitable polyepoxides include, for example, polyepoxide resins such as hydantoin diepoxide, diglycidyl ether of bisphenol-A, diglycidyl ether of bisphenol-F, Novolac® type epoxides such as DEN™ 438 (Dow Chemical Company), certain epoxidized unsaturated resins, and combinations of any of the foregoing. A polyepoxide refers to a compound having two or more reactive epoxy groups. An epoxide curing agent is selected from EPON™ 828 (Momentive Specialty Chemicals, Inc), DEN™ 431 (Dow Chemical Company), and a combination thereof. Examples of useful curing agents that are reactive with thiol groups include diepoxides.

A polyepoxy curing agent may comprise an epoxy-functional prepolymer. Examples of suitable epoxy-functional prepolymers include the epoxy-functional sulfur-containing polyformal prepolymers disclosed in U.S. Application Publication No. 2012/0238708 and epoxy-functional polythioether prepolymers disclosed in U.S. Pat. No. 7,671,145. In general, when used as a curing agent, an epoxy-functional prepolymer has a molecular weight less than about 2,000 Daltons, less than about 1,500, Daltons, less than about 1,000 Daltons, or less than about 500 Daltons.

A polyepoxy may comprise about 0.5 wt % to about 20 wt % of the composition, from about 1 wt % to about 10 wt %, from about 2 wt % to about 8 wt %, from about 2 wt % to about 6 wt %, and in or from about 3 wt % to about 5 wt %, where wt % is based on the total solids weight of the composition.

In compositions containing a reactive antioxidant terminated with thiol groups, a suitable curing agent can also be an unsaturated compound such as an acrylic or methacrylic ester of a polyol, unsaturated synthetic or naturally occurring resin compounds, triallyl cyanurate, and olefin terminated derivatives of sulfur-containing compound such as polythioethers.

In compositions containing an amine and/or hydroxyl-terminated reactive antioxidant or antioxidant-containing prepolymer the composition may comprise an isocyanate curing agent such as a diisocyanate and/or triisocyanate curing agent. Examples of suitable isocyanate curing agents include toluene diisocyanate, and combinations of any of the foregoing. Isocyanate curing agents are commercially available and include, for example, products under the tradenames Baydur® (Bayer MaterialScience), Desmodur® (Bayer MaterialScience), Solubond® (DSM), ECCO (ECCO), Vestanat® (Evonik), Irodur® (Huntsman), Rhodocoat™ (Perstorp), and Vanchem® (V.T. Vanderbilt). A polyisocyanate curing agent can comprise isocyanate groups that are reactive with thiol groups and that are less reactive with Michael acceptor groups. Examples of useful curing agents that are reactive with amine groups include polymeric polyisocyanates, non-limiting examples of which include polyisocyanates having backbone linkages chosen from urethane linkages (—NH—C(O)—O—), thiourethane linkages (—NH—C(O)—S—), thiocarbamate linkages (—NH—C(S)—O—), dithiourethane linkages (—NH—C(S)—S—), and combinations of any of the foregoing.

An isocyanate curing agent can comprise an isocyanate-functional polymer. Examples of suitable isocyanate-functional polymers include the isocyanate-functional sulfur-containing polyformal polymers disclosed in U.S. Application Publication No. 2012/0238708. In general, when used as a curing agent, an isocyanate-functional polymer can have a molecular weight less than about 2,000

Daltons, less than about 1,500, Daltons, less than about 1,000 Daltons, or less than about 500 Daltons.

In such compositions, an isocyanate curing agent may comprise about 0.5 wt % to about 20 wt % of the composition, from about 1 wt % to about 10 wt %, from about 2 wt % to about 8 wt %, from about 2 wt % to about 6 wt %, or from about 3 wt % to about 5 wt % of the composition, where wt % is based on the total solids weight of the composition.

In compositions having an isocyanate-terminated reactive antioxidant and/or antioxidant-containing prepolymer a composition may comprise an amine curing agent. Examples of useful curing agents that are reactive with isocyanate groups include diamines, polyamines, polythiols, and polyols, including those disclosed herein.

In compositions having a Michael acceptor-terminated reactive antioxidant and/or antioxidant-containing prepolymer the composition may comprise a curing agent selected from a monomeric thiol, a polythiol, a polyamine, and a blocked polyamine.

Examples of useful curing agents that are reactive with hydroxyl groups include diisocyanates and polyisocyanates, examples of which are disclosed herein.

Examples of useful curing agents that are reactive with alkenyl groups include dithiols and polythiols, examples of which are disclosed herein.

Polyalkoxysilyl-terminated reactive antioxidants and antioxidant-containing prepolymers provided by the present disclosure can hydrolyze in the presence of water inducing self-polymerization via condensation. Catalysts for use with polyalkoxysilyl-terminated bis(sulfonyl)alkanol-containing polythioether or polyalkoxysilyl-terminated metal ligand-containing prepolymer, include organotitanium compounds such as tetraisopropoxy titanium, tetra-tert-butoxy titanium, titanium di(isopropoxy)bis(ethylacetoacetate), and titanium di(isopropoxy)bis(acetylacetoacetate); organic tin compounds dibutyltin dilaurate, dibutyltin bisacetylacetoacetate, and tin octylate; metal dicarboxylates such as lead dioctylate; organozirconium compounds such as zirconium tetraacetyl acetonate; and organoaluminum compounds such as aluminum triacetyl-acetonate. Other examples of suitable catalysts for moisture curing include diisopropoxy bis(ethyl acetoacetonate)titanium, diisopropoxy bis(acetyl acetonate) titanium, and dibutoxy bis(methyl acetoacetonate)titanium. It can be appreciated that because the curing agent for polyalkoxysilyl-terminated bis(sulfonyl)alkanol-containing polythioether or polyalkoxysilyl-terminated metal ligand-containing prepolymer, can be atmospheric moisture, it is not necessary to include a curing agent to a curable composition containing polyalkoxysilyl-terminated bis(sulfonyl) alkanol-containing polythioether or polyalkoxysilyl-terminated metal ligand-containing prepolymer. Therefore, compositions comprising polyalkoxysilyl-terminated reactive antioxidants and/or antioxidant-containing prepolymers and a curing agent for the polyalkoxysilyl group refer to atmospheric moisture.

In compositions comprising reactive antioxidants and/or antioxidant-containing prepolymers terminated with epoxy groups, a suitable curing agent is a polythiol, polyalkylene, or polyamine. Other examples of useful curing agents that are reactive with terminal epoxy groups include amines such as diethylenetriamine (DTA), triethylenetetramine (TTA), tetraethylenepentamine (TEPA), diethylaminopropylamine (DEAPA), N-aminoethylpiperazine (N-AEP), isophoronediamine (IPDA), m-xylenediamine, diaminodiphenylmethane (DDM), diaminodiphenylsulfone (DDS); aromatic amines; ketimine; polyamines; polyamides; phenolic resins; anhydrides such phthalic anhydride, trimellitic anhydride, pyromellitic anhydride, benzophenone tetracarboxylic anhydride, ethylene glycol bistrimellitate, glycerol tristrimellitate, maleic anhydride, tetrahydrophthalic anhydride, methyltetrahydrophthalic anhydride, endomethylene tetrahydrophthalic anhydride; polymercaptans; polysulfides; and other curing agents known to those skilled in the art.

Compositions provided by the present disclosure may contain from about 90% to about 150% of the stoichiometric amount, from about 95% to about 125%, or from about 95% to about 105% of the amount of the selected curing agent(s).

Additional Sulfur-Containing Prepolymers

Compositions provided by the present disclosure may comprise, in addition to a reactive antioxidant and/or antioxidant-containing prepolymer, one or more additional sulfur-containing prepolymers. An additional sulfur-containing prepolymer can be any prepolymer having at least one sulfur atom in the repeating unit, including, but not limited to, polymeric thiols, polythiols, thioethers, polythioethers, sulfur-containing polyformals, and polysulfides. A "thiol," as used herein, refers to a compound comprising a thiol or mercaptan group, that is, an "SH" group, either as the sole functional group or in combination with other functional groups, such as hydroxyl groups, as is the case with, for example, thioglycerols. A polythiol refers to such a compound having more than one SH group, such as a dithiol or higher functionality thiol. Such groups are typically terminal and/or pendant such that they have an active hydrogen that is reactive with other functional groups. A polythiol can comprise both a terminal and/or pendant sulfur (—SH) and a non-reactive sulfur atom (—S— or —S—S—). Thus, the term polythiol generally encompasses polythioethers and polysulfides.

Examples of additional sulfur-containing prepolymers useful in compositions provided by the present disclosure include, for example, those disclosed in U.S. Pat. Nos. 6,172,179; 6,509,418; and 7,009,032. Compositions provided by the present disclosure comprise a polythioether comprising a backbone having the structure of Formula (10):

—R$^1$—[—S—(CH$_2$)$_2$—O—[—R$^2$—O—]$_m$— (CH$_2$)$_2$—S—R$^1$—]$_n$— (10)

wherein R$^1$ is selected from a C$_{2-6}$ alkanediyl, C$_{6-8}$ cycloalkanediyl, C$_{6-10}$ cycloalkanealkanediyl, —[(—CH$_2$—)$_p$—X—]$_q$—(—CH$_2$—)$_r$—, and —[(—CH$_2$—)$_p$—X—]$_q$—(—CH$_2$—)$_r$— in which at least one —CH$_2$— unit is substituted with a methyl group; R$^2$ is selected from C$_{2-6}$ alkanediyl, C$_{6-8}$ cycloalkanediyl, C$_{6-10}$ cycloalkanealkanediyl, and —[(—CH$_2$—)$_p$—X—]$_q$—(—CH$_2$—)$_r$—; X is selected from O, S, and —NR$^5$—, where R$^5$ is selected from hydrogen and methyl; m is an integer from 0 to 10; n is an integer from 1 to 60; p is an integer from 2 to 6; q is an integer from 1 to 5, and r is an integer from 2 to 10. Such polythioethers are described in U.S. Pat. No. 6,172,179 at col. 2, line 29 to col. 4, line 34.

The one or more additional sulfur-containing prepolymers may be difunctional or multifunctional, for example, having from 3 to 6 terminal groups, or a mixture of difunctional and multifunctional sulfur-containing prepolymers.

Compositions provided by the present disclosure comprise from about 10 wt % to about 90 wt % of a reactive antioxidant and/or antioxidant-containing prepolymer provided by the present disclosure, from about 20 wt % to about 80 wt %, from about 30 wt % to about 70 wt %, or from about 40 wt % to about 60 wt %, where wt % is based on the total weight of all non-volatile components of the composition (i.e., the dry weight).

Compositions provided by the present disclosure may contain a reactive antioxidant and a sulfur-containing prepolymer that does not incorporate antioxidants. The composition may contain, for example, from 1 wt % to 50 wt %, from 1 wt % to 30 wt %, from 1 wt % to 20 wt %, or from 1 wt % to 10 wt % of a reactive antioxidant, where wt % is based on the total weight of the reactive antioxidant and the sulfur-containing prepolymer.

A reactive antioxidant and/or antioxidant-containing polythioether prepolymer may comprise from about 50 wt % to about 90 wt % of a composition, from about 60 wt % to about 90 wt %, from about 70 wt % to about 90 wt %, or from about 80 wt % to about 90 wt % of the composition, where wt % is based on the total dry solids weight of the composition.

An sulfur-containing prepolymer can be selected from a polythioether and a polysulfide, and a combination thereof. A sulfur-containing prepolymer can comprise a polythioether, or a sulfur-containing prepolymer can comprise a polysulfide. A sulfur-containing prepolymer may comprise a mixture of different polythioethers and/or polysulfides, and the polythioethers and/or polysulfides may have the same or different functionality. A sulfur-containing prepolymer can have an average functionality from 2 to 6, from 2 to 4, from 2 to 3, or from 2.05 to 2.5. For example, a sulfur-containing prepolymer can be selected from a difunctional sulfur-containing prepolymer, a trifunctional sulfur-containing prepolymer, and a combination thereof.

Compositions provided by the present disclosure may include one or more catalysts. A catalyst can be selected as appropriate for the curing chemistry employed. For example, when curing thiol-terminated antioxidant-containing polythioether prepolymers and polyepoxides, the catalyst can be an amine catalyst. A cure catalyst may be present in an amount from 0.1 to 5 weight percent, based on the total weight of the composition. Examples of suitable catalysts include 1,4-diazabicyclo[2.2.2]octane (DABCO®, commercially available from Air Products, Chemical Additives Division, Allentown, Pa.) and DMP-30® (an accelerant composition including 2,4,6-tris(dimethylaminomethyl) phenol).

Compositions provided by the present disclosure can comprise one or more than one adhesion promoters. A one or more additional adhesion promoter may be present in amount from 0.1 wt % to 15 wt % of a composition, less than 5 wt %, less than 2 wt %, or less than 1 wt %, based on the total dry weight of the composition. Examples of adhesion promoters include phenolics, such as Methylon® phenolic resin, and organosilanes, such as epoxy, mercapto or amino functional silanes, such as Silquest® A-187 and Silquest® A-1100. Other useful adhesion promoters are known in the art.

Compositions provided by the present disclosure may comprise one or more different types of filler. Suitable fillers include those commonly known in the art, including inorganic fillers, such as carbon black and calcium carbonate ($CaCO_3$), silica, polymer powders, and lightweight fillers. Suitable lightweight fillers include, for example, those described in U.S. Pat. No. 6,525,168. A composition can include 5 wt % to 60 wt % of the filler or combination of fillers, 10 wt % to 50 wt %, or from 20 wt % to 40 wt %, based on the total dry weight of the composition. Compositions provided by the present disclosure may further include one or more colorants, thixotropic agents, accelerators, fire retardants, adhesion promoters, solvents, masking agents, or a combination of any of the foregoing. As can be appreciated, fillers and additives employed in a composition may be selected so as to be compatible with each other as well as the polymeric component, curing agent, and or catalyst. Examples of electrically non-conductive fillers include materials such as, but not limited to, calcium carbonate, mica, polyamide, fumed silica, molecular sieve powder, microspheres, titanium dioxide, chalks, alkaline blacks, cellulose, zinc sulfide, heavy spar, alkaline earth oxides, alkaline earth hydroxides, and the like.

Compositions provided by the present disclosure can comprise low density filler particles. As used herein, low density, when used with reference to such particles means that the particles have a specific gravity of no more than 0.7, no more than 0.25, or no more than 0.1. Suitable lightweight filler particles often fall within two categories—microspheres and amorphous particles. The specific gravity of microspheres may range from 0.1 to 0.7 and include, for example, polystyrene foam, microspheres of polyacrylates and polyolefins, and silica microspheres having particle sizes ranging from 5 to 100 microns and a specific gravity of 0.25 (Eccospheres®). Other examples include alumina/silica microspheres having particle sizes in the range of 5 to 300 microns and a specific gravity of 0.7 (Fillite®), aluminum silicate microspheres having a specific gravity of from about 0.45 to about 0.7 (Z-Light?), calcium carbonate-coated polyvinylidene copolymer microspheres having a specific gravity of 0.13 (Dualite® 6001AE), and calcium carbonate coated acrylonitrile copolymer microspheres such as Dualite® E135, having an average particle size of about 40 μm and a density of 0.135 g/cc (Henkel). Suitable fillers for decreasing the specific gravity of the composition include, for example, hollow microspheres such as Expancel® microspheres (available from AkzoNobel) or Dualite® low density polymer microspheres (available from Henkel). Compositions provided by the present disclosure include lightweight filler particles comprising an exterior surface coated with a thin coating, such as those described in U.S. Application Publication No. 2010/0041839 at paragraphs [0016]-[0052], the cited portion of which is incorporated herein by reference.

A composition an comprise less than 2 wt % of a low density filler, less than 1.5 wt %, less than 1.0 wt %, less than 0.8 wt %, less than 0.75 wt %, less than 0.7 wt %, or less than 0.5 wt % of a low density filler, where wt % is based on the total dry solids weight of the composition.

Compositions provided by the present disclosure can comprise at least one filler that is effective in reducing the specific gravity of the composition. The specific gravity of a composition is from 0.8 to 1, 0.7 to 0.9, from 0.75 to 0.85, or can be 0.8. The specific gravity of a composition is less than about 0.9, less than about 0.8, less than about 0.75, less than about 0.7, less than about 0.65, less than about 0.6, or, less than about 0.55.

Compositions provided by the present disclosure can comprise an electrically conductive filler. Electrical conductivity and EMI/RFI shielding effectiveness can be imparted to composition by incorporating conductive materials within the polymer. The conductive elements can include, for example, metal or metal-plated particles, fabrics, meshes, fibers, and combinations thereof. The metal can be in the form of, for example, filaments, particles, flakes, or spheres. Examples of metals include copper, nickel, silver, aluminum, tin, and steel. Other conductive materials that can be used to impart electrical conductivity and EMI/RFI shielding effectiveness to polymer compositions include conductive particles or fibers comprising carbon or graphite. Conductive polymers such as polythiophenes, polypyrroles, polyaniline, poly(p-phenylene) vinylene, polyphenylene sulfide, polyphenylene, and polyacetylene can also be used. Electrically conductive fillers also include high band gap materials such as zinc sulfide and inorganic barium compounds.

Other examples of electrically conductive fillers include electrically conductive noble metal-based fillers such as pure silver; noble metal-plated noble metals such as silver-plated gold; noble metal-plated non-noble metals such as silver plated cooper, nickel or aluminum, for example, silver-plated aluminum core particles or platinum-plated copper particles; noble-metal plated glass, plastic or ceramics such as silver-plated glass microspheres, noble-metal plated aluminum or noble-metal plated plastic microspheres; noble-metal plated mica; and other such noble-metal conductive fillers. Non-noble metal-based materials can also be used and include, for example, non-noble metal-plated non-noble metals such as copper-coated iron particles or nickel plated copper; non-noble metals, e.g., copper, aluminum, nickel, cobalt; non-noble-metal-plated-non-metals, e.g., nickel-plated graphite and non-metal materials such as carbon black and graphite. Combinations of electrically conductive fillers can also be used to meet the desired conductivity, EMI/RFI shielding effectiveness, hardness, and other properties suitable for a particular application.

The shape and size of the electrically conductive fillers used in the compositions of the present disclosure can be any appropriate shape and size to impart electrical conductivity and EMI/RFI shielding effectiveness to the cured composition. For example, fillers can be of any shape generally used in the manufacture of electrically conductive fillers, including spherical, flake, platelet, particle, powder, irregular, fiber, and the like. In certain sealant compositions of the disclosure, a base composition can comprise Ni-coated graphite as a particle, powder or flake. The amount of Ni-coated graphite in a base composition can range from 40 wt % to 80 wt %, or can range from 50 wt % to 70 wt %, based on the total weight of the base composition. An electrically conductive filler can comprise Ni fiber. Ni fiber can have a diameter ranging from 10 µm to 50 µm and have a length ranging from 250 µm to 750 µm. A base composition can comprise, for example, an amount of Ni fiber ranging from 2 wt % to 10 wt %, or from 4 wt % to 8 wt %, based on the total weight of the base composition.

Carbon fibers, particularly graphitized carbon fibers, can also be used to impart electrical conductivity to compositions of the present disclosure. Carbon fibers formed by vapor phase pyrolysis methods and graphitized by heat treatment and which are hollow or solid with a fiber diameter ranging from 0.1 micron to several microns, have high electrical conductivity. As disclosed in U.S. Pat. No. 6,184, 280, carbon microfibers, nanotubes or carbon fibrils having an outer diameter of less than 0.1 µm to tens of nanometers can be used as electrically conductive fillers. An example of graphitized carbon fiber suitable for conductive compositions of the present disclosure include Panex® 3OMF (Zoltek Companies, Inc., St. Louis, Mo.), a 0.921 µm diameter round fiber having an electrical resistivity of 0.00055 Ωcm.

The average particle size of an electrically conductive filler can be within a range useful for imparting electrical conductivity to a polymer-based composition. For example, the particle size of the one or more fillers can range from 0.25 µm to 250 µm, can range from 0.25 µm to 75 µm, or can range from 0.25 µm to 60 µm. Composition provided by the present disclosure can comprise Ketjenblack® EC-600 JD (Akzo Nobel, Inc., Chicago, Ill.), an electrically conductive carbon black characterized by an iodine absorption of 1,000 mg/g to 11,500 mg/g (J0/84-5 test method), and a pore volume of 480 cm$^3$/100 g to 510 cm$^3$/100 g (DBP absorption, KTM 81-3504). An electrically conductive carbon black filler is Black Pearls® 2000 (Cabot Corporation, Boston, Mass.).

Electrically conductive polymers can be used to impart electrical conductivity or modify the electrical conductivity of compositions of the present disclosure. Polymers having sulfur atoms incorporated into aromatic groups or adjacent to double bonds, such as in polyphenylene sulfide, and polythiophene, are known to be electrically conductive. Other electrically conductive polymers include, for example, polypyrroles, polyaniline, poly(p-phenylene) vinylene, and polyacetylene. The sulfur-containing prepolymers forming a base composition can be polysulfides and/or polythioethers. As such, the sulfur-containing prepolymers can comprise aromatic sulfur groups and sulfur atoms adjacent to conjugated double bonds to enhance the electrical conductivity of the compositions of the present disclosure.

Compositions of the present disclosure can comprise more than one electrically conductive filler and the more than one electrically conductive filler can be of the same or different materials and/or shapes. For example, a sealant composition can comprise electrically conductive Ni fibers, and electrically conductive Ni-coated graphite in the form of powder, particles or flakes. The amount and type of electrically conductive filler can be selected to produce a sealant composition which, when cured, exhibits a sheet resistance (four-point resistance) of less than 0.50 Ω/cm$^2$, or a sheet resistance less than 0.15 Ω/cm$^2$. The amount and type of filler can also be selected to provide effective EMI/RFI shielding over a frequency range of from 1 MHz to 18 GHz for an aperture sealed using a sealant composition of the present disclosure.

An electrically conductive base composition can comprise an amount of electrically non-conductive filler ranging from 2 wt % to 10 wt % based on the total weight of the base composition, or can range from 3 wt % to 7 wt %. A curing agent composition can comprise an amount of electrically non-conductive filler ranging from less than 6 wt % or ranging from 0.5% to 4% by weight, based on the total weight of the curing agent composition.

Galvanic corrosion of dissimilar metal surfaces and the conductive compositions of the present disclosure can be minimized or prevented by adding corrosion inhibitors to the composition, and/or by selecting appropriate conductive fillers. Corrosion inhibitors can include strontium chromate, calcium chromate, magnesium chromate, and combinations thereof. U.S. Pat. No. 5,284,888 and U.S. Pat. No. 5,270,364 disclose the use of aromatic triazoles to inhibit corrosion of aluminum and steel surfaces. A sacrificial oxygen scavenger such as Zn can be used as a corrosion inhibitor. A corrosion inhibitor can comprise less than 10% by weight of the total weight of the electrically conductive composition. A corrosion inhibitor can comprise an amount ranging from 2 wt % to 8 wt % of the total weight of the electrically conductive composition. Corrosion between dissimilar metal surfaces can also be minimized or prevented by the selection of the type, amount, and properties of the conductive fillers comprising the composition.

A composition may also include any number of additives as desired. Examples of suitable additives include plasticizers, pigments, surfactants, adhesion promoters, thixotropic agents, fire retardants, masking agents, and accelerators (such as amines, including 1,4-diazabicyclo[2.2.2] octane, DABCO®), and combinations of any of the foregoing. When used, the additives may be present in a composition in an amount ranging, for example, from about 0.5% to 60% by weight, where wt % is based on the total solids weight of the composition. Additives may be present in a composition in an amount ranging from about 25 wt % to 60 wt %.

Uses

Compositions provided by the present disclosure may be used, for example, in sealants, coatings, encapsulants, and potting compositions. A sealant includes a composition capable of producing a film that has the ability to resist operational conditions, such as moisture and temperature, and at least partially block the transmission of materials, such as water, fuel, and other liquid and gases. A coating composition includes a covering that is applied to the surface of a substrate to, for example, improve the properties of the substrate such as the appearance, adhesion, wettability, corrosion resistance, wear resistance, fuel resistance, and/or abrasion resistance. A potting composition includes a material useful in an electronic assembly to provide resistance to shock and vibration and to exclude moisture and corrosive agents. Sealant compositions provided by the present disclosure are useful, e.g., as aerospace sealants and as linings for fuel tanks.

Compositions, such as sealants, may be provided as multi-pack compositions, such as two-pack compositions, wherein one package comprises one or more reactive antioxidants and/or antioxidant-containing prepolymers provided by the present disclosure and a second package comprises one or more polyfunctional sulfur-containing epoxies provided by the present disclosure. Additives and/or other materials may be added to either package as desired or as necessary. The two packages may be combined and mixed prior to use. The pot life of the one or more mixed reactive antioxidants and/or antioxidant-containing prepolymers and epoxides is at least 30 minutes, at least 1 hour, at least 2 hours, or more than 2 hours, where pot life refers to the period of time the mixed composition remains suitable for use as a sealant after mixing.

Compositions, including sealants, provided by the present disclosure may be applied to any of a variety of substrates. Examples of substrates to which a composition may be applied include metals such as titanium, stainless steel, aluminum, and alloys thereof, any of which may be anodized, primed, organic-coated or chromate-coated; epoxy; urethane; graphite; fiberglass composite; Kevlar®; acrylics; and polycarbonates. Compositions provided by the present disclosure may be applied to a coating on a substrate, such as a polyurethane coating. Compositions comprising antioxidant-containing polythioethers or antioxidant-containing prepolymers provided by the present disclosure exhibit enhanced adhesion to aluminum, aluminum oxide, anodized aluminum, titanium, titanium oxide, and/or Alodine® surfaces, compared to similar compositions without an antioxidant.

Compositions provided by the present disclosure may be applied directly onto the surface of a substrate or over an underlayer by any suitable coating process known to those of ordinary skill in the art.

Furthermore, methods are provided for sealing a part using a composition provided by the present disclosure. These methods comprise, for example, applying a composition provided by the present disclosure to a surface of a part, and curing the composition. For example, methods of sealing a part, comprise preparing a curable composition comprising the a reactive antioxidant or antioxidant-containing prepolymer provided by the present disclosure, applying the curable composition to a part; and curing the curable composition to seal the part.

Parts sealed with a sealant composition of the present disclosure are provided.

A composition may be cured under ambient conditions, where ambient conditions refers to a temperature from 20° C. to 25° C., and atmospheric humidity. A composition may be cured under conditions encompassing a temperature from a 0° C. to 100° C. and humidity from 0% relative humidity to 100% relative humidity. A composition may be cured at a higher temperature such as at least 30° C., at least 40° C., or at least 50° C. A composition may be cured at room temperature, e.g., 25° C. A composition may be cured upon exposure to actinic radiation, such as ultraviolet radiation. As will also be appreciated, the methods may be used to seal apertures on aerospace vehicles including aircraft and aerospace vehicles.

Ae composition can achieve a tack-free cure in less than about 2 hours, less than about 4 hours, less than about 6 hours, less than about 8 hours, or less than about 10 hours, at a temperature of less than about 200° F.

The time to form a viable seal using curable compositions of the present disclosure can depend on several factors as can be appreciated by those skilled in the art, and as defined by the requirements of applicable standards and specifications. In general, curable compositions of the present disclosure develop adhesion strength within 24 hours to 30 hours, and 90% of full adhesion strength develops from 2 days to 3 days, following mixing and application to a surface. In general, full adhesion strength as well as other properties of cured compositions of the present disclosure becomes fully developed within 7 days following mixing and application of a curable composition to a surface.

Cured compositions disclosed herein, such as cured sealants, exhibit properties acceptable for use in aerospace applications. In general, it is desirable that sealants used in aviation and aerospace applications exhibit the following properties: peel strength greater than 20 pounds per linear inch (pli) on Aerospace Material Specification (AMS) 3265B substrates determined under dry conditions, following immersion in Jet Reference Fluid (JRF) Type I for 7 days, and following immersion in a solution of 3% NaCl according to AMS 3265B test specifications; tensile strength between 300 pounds per square inch (psi) and 400 psi; tear strength greater than 50 pounds per linear inch (pli); elongation between 250% and 300%; and hardness greater than 40 Durometer A. These and other cured sealant properties appropriate for aviation and aerospace applications are disclosed in AMS 3265B, the entirety of which is incorporated herein by reference. It is also desirable that, when cured, compositions of the present disclosure used in aviation and aircraft applications exhibit a percent volume swell not greater than 25% following immersion for one week at 60° C. (140° F.) and ambient pressure in JRF Type I. Other properties, ranges, and/or thresholds may be appropriate for other sealant applications.

Compositions provided by the present disclosure can be fuel-resistant. As used herein, the term "fuel resistant" means that a composition, when applied to a substrate and cured, can provide a cured product, such as a sealant, that exhibits a percent volume swell of not greater than 40%, in some cases not greater than 25%, in some cases not greater than 20%, in yet other cases not more than 10%, after immersion for one week at 140° F. (60° C.) and ambient pressure in Jet Reference Fluid (JRF) Type I according to methods similar to those described in ASTM D792 (American Society for Testing and Materials) or AMS 3269 (Aerospace Material Specification). Jet Reference Fluid JRF Type I, as employed for determination of fuel resistance, has the following composition: toluene: 28%±1% by volume; cyclohexane (technical): 34%±1% by volume; isooctane: 38%±1% by volume; and tertiary dibutyl disulfide: 1%±0.005% by volume (see AMS 2629, issued Jul. 1, 1989, §3.1.1, etc., available from SAE (Society of Automotive Engineers)).

Compositions provided herein can provide a cured product, such as a sealant, exhibiting a elongation of at least 100% and a tensile strength of at least 400 psi when measured in accordance with the procedure described in AMS 3279, §3.3.17.1, test procedure AS5127/1, §7.7.

Compositions can provide a cured product, such as a sealant, that exhibits a lap shear strength of greater than 200 psi, such as at least 220 psi, at least 250 psi, and, in some cases, at least 400 psi, when measured according to the procedure described in SAE AS5127/1 paragraph 7.8.

A cured sealant comprising a composition provided by the present disclosure can meet or exceed the requirements for aerospace sealants as set forth in AMS 3277.

Apertures, including apertures of aerospace vehicles, sealed with compositions provided by the present disclosure are also disclosed.

A cured sealant provided by the present disclosure can exhibit the following properties when cured for 2 days at room temperature, 1 day at 140° F. and 1 day at 200° F.: a dry hardness of 49, a tensile strength of 428 psi, and an elongation of 266%; and after 7 days in JRF Type I, a hardness of 36, a tensile strength of 312 psi, and an elongation of 247%.

Compositions provided by the present disclosure can exhibit a Shore A hardness (7-day cure) greater than 10, greater than 20, greater than 30, or greater than 40; a tensile strength greater than 10 psi, greater than 100 psi, greater than 200 psi, or greater than 500 psi; an elongation greater than 100%, greater than 200%, greater than 500%, or greater than 1,000%; and a swell following exposure to JRF Type I (7 days) less than 20%.

EXAMPLES

Aspects of present invention are further illustrated by reference to the following examples, which describe the synthesis, properties, and uses of certain reactive antioxidants and antioxidant-containing sulfur-containing prepolymers, compositions comprising reactive antioxidants and/or antioxidant-containing sulfur-containing prepolymers, and cured sealants prepared using compositions comprising reactive antioxidants and/or antioxidant-containing sulfur-containing prepolymers. It will be apparent to those skilled in the art that many modifications, both to materials, and methods, may be practiced without departing from the scope of the disclosure.

Example 1

Synthesis of Curable Reactive Antioxidant Prepared from 1,8-Dimercapto-3,6-Dioxaoctane (DMDO) and 3,5-Di-tert-Butyl-4-Hydroxybenzaldehyde Hemihydrate; Dithiol Aldehyde Ratio: 2:1

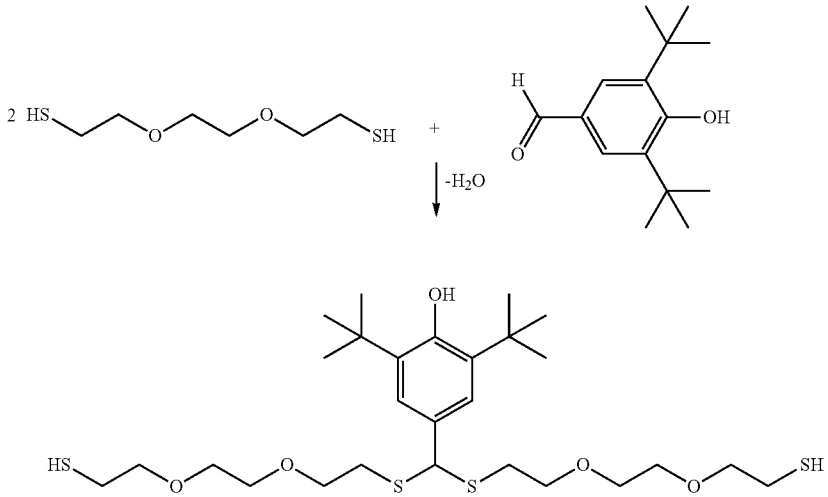

3,5-Di-tert-butyl-4-hydroxybenzaldehyde hemihydrate (9.07 g, 0.037 mole), solid acid catalyst Amberlyst® 15 (1.02 g) and tetrahydrofuran (THF; 18 g) were charged into a 100-mL 3-necked round-bottomed flask. The flask was equipped with a mechanical stirrer, a gas adapter and a temperature probe. While stirring, DMDO (13.58 g; 0.074 moles) was added into the heterogeneous solution (temp.: 19.2° C.). A mild exotherm started immediately and the solid began to disappear. In 30 min, the temperature rose to 30° C. and the reaction mixture became dark red and homogeneous. After 4 h of additional stirring, IR analysis of the supernatant solution confirmed the absence of an aldehyde signal (1666 cm$^{-1}$).

The reaction mixture was stirred further at room temperature for 17 h. The flask was equipped with a reflux condenser and contents were then heated at 66° C. for 9 h. After cooling to room temperature, the reaction mixture was filtered through a sintered funnel (porosity: 5 micron). Removal of residual volatiles provided the title compound as a red liquid (mercaptan equivalent weight: 240; viscosity: 4.75P; theoretical functionality: 2.0).

Example 2

Synthesis of Curable Reactive Antioxidant (MW: 998) Prepared from DMDO and 3,5-Di-tert-Butyl-4-Hydroxybenzaldehyde Hemihydrate; Dithiol Aldehyde Ratio: 3:2

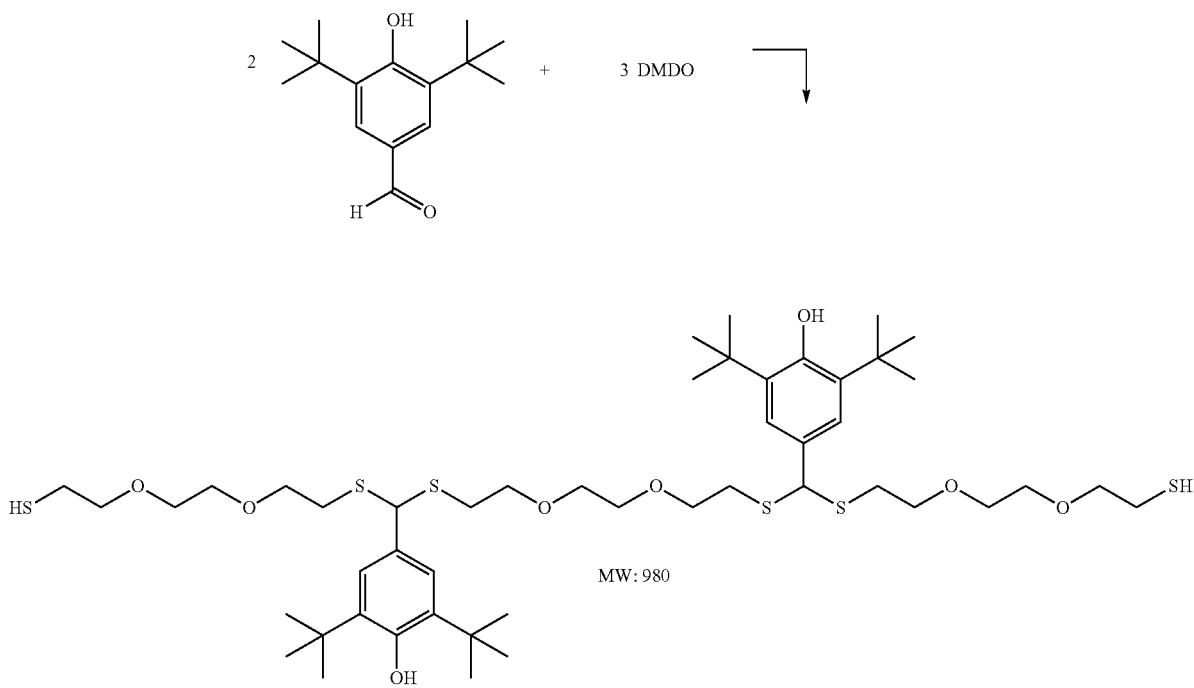

3,5-Di-tert-butyl-4-hydroxybenzaldehyde hemihydrate (9.73 g, 0.04 mole), solid acid catalyst Amberlyst® 15 (0.93 g) and tetrahydrofuran (20 g) were charged into a 100-mL 3-necked round-bottomed flask. The flask was equipped with a magnetic stir bar, a gas adapter and a temperature probe. While stirring, DMDO (10.94 g; 0.06 moles) was added into the heterogeneous solution (temp.: 19° C.). A mild exotherm started immediately and the solid began to disappear. Within 5 min, the temperature rose to 30° C. and the reaction mixture became dark red and homogeneous. After 17 h of additional stirring, IR analysis of the supernatant solution confirmed the absence of aldehyde signal (1666 cm$^{-1}$).

The flask was equipped with a reflux condenser. The reaction mixture was heated at 66° C. for 14 h, cooled to room temperature, and filtered through a sintered funnel (porosity: 5 micron). Removing the volatiles provided the title compound as a viscous red liquid (mercaptan equivalent weight: 495; viscosity: 358P; theoretical functionality: 2.0).

Example 3

Synthesis of a Trithiol from Triallyl Cyanurate (TAC) and DMDO

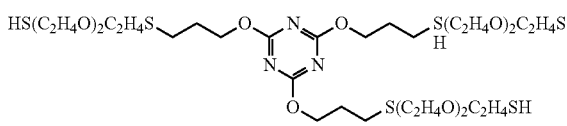

Triallyl cyanurate (TAC) (49.86 g; 0.02 mole) was charged into a 250-mL 3-necked round-bottomed flask. The flask was equipped with a mechanical stirrer and a gas-adapter. The contents were flushed with nitrogen. While stirring, DMDO was added, and the contents were stirred for 2.5 h.

The reaction mixture was heated to 70° C. and five portions of radical initiator Vazo®-67 (each: 0.029 g; 0.00015 mole) were added at an interval of 1 h. Evacuation of the reaction mixture (70° C./17 mm for 2 h) provided the title compound as a clear liquid trithiol (mercaptan equivalent weight: 277; viscosity: 55P).

Example 4

Synthesis of a Tetrafunctional Reactive Antioxidant Prepared from a Trithiol and 3,5-Di-tert-Butyl-4-Hydroxybenzaldehyde Hemihydrate

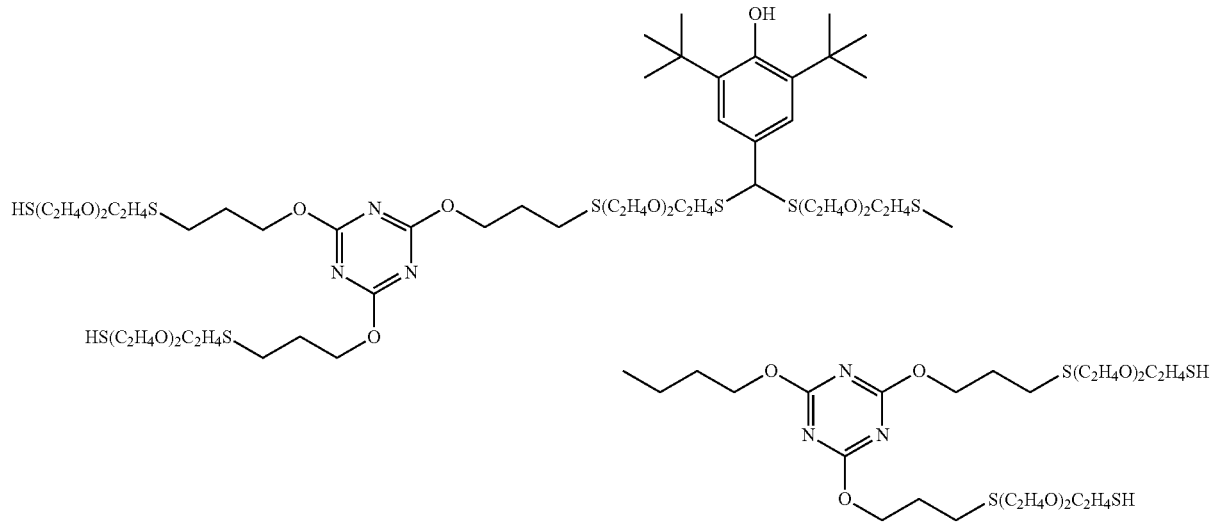

The trithiol of Example 3 (75.99 g, 0.091 moles) and acid catalyst Amberlyst® 15 (3.92 g) were charged into a 250-mL 3-necked round-bottomed flask. The flask was equipped with a mechanical stirrer and a gas adapter. The contents were flushed with nitrogen and the flask was equipped with a temperature probe. While stirring, 3,5-di-tert-butyl-4-hydroxybenzaldehyde hemihydrate (11.13 g, 0.0457 moles) was introduced in portions (temp.: 19.2° C.). Tetrahydrofuran (47 g) was used to wash the solid aldehyde into the reaction mixture. The solid had dissolved in 1.5 h.

The reaction mixture was stirred at room temperature for 15 h and the viscosity of the reaction mixture increased. The flask was equipped with a reflux condenser and heated to 66° C. At 55° C., the reaction mixture started to curl up along the stirrer-shaft. Tetrahydrofuran (40 g) was introduced to reduce the viscosity of the reaction mixture. A small ball of solid material was observed in the reaction mixture and broken into pieces. The mixture was reacted at 66° C. for 10 h. After cooling to room temperature, the reaction mixture was filtered through a sintered funnel (porosity: ~4.5-5 microns). Tetrahydrofuran (4 portions; 25 mL each) was used to wash the catalyst-beads and the filtration assembly. The supernatant was combined with the filtrate. After removing the volatiles, the title compound as a light brown cloudy solid was obtained (mercaptan equivalent weight: 427; theoretical functionality: 4.0). The cloudiness was associated with the presence of very fine off-white solid particles.

Example 5

Synthesis of a Trifunctional Reactive Antioxidant Prepared from 3,5-Di-tert-Butyl-4-Hydroxybenzaldehyde Hemihydrate and a Mixture of Dithiol (DMDO) and Trithiol

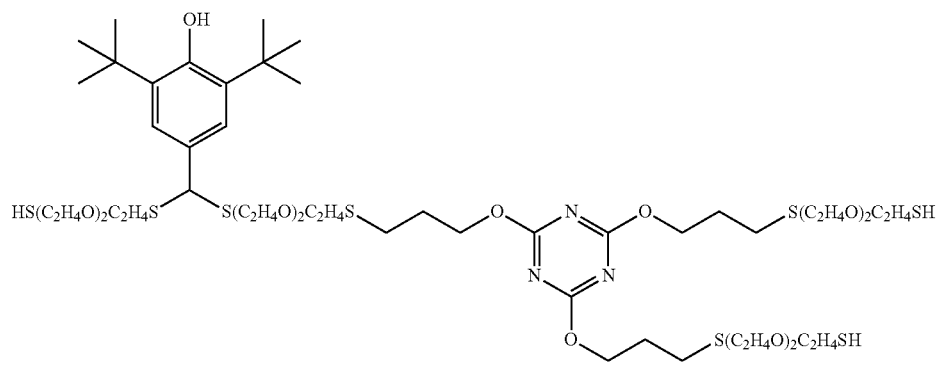

The trithiol of Example 3 (38 g, 0.0457 moles), DMDO (8.34 g, 0.0457 moles) and acid catalyst Amberlyst® 15

(2.21 g) were charged into a 250-mL 3-necked round-bottomed flask. The flask was equipped with a mechanical stirrer, a gas adapter and a temperature probe. While stirring, 3,5-di-tert-butyl-4-hydroxybenzaldehyde hemihydrate (11.13 g, 0.0457 moles) was introduced in portions (temp.: 24° C.). Tetrahydrofuran (26 g) was used to wash the solid aldehyde into the reaction mixture.

The solid aldehyde had dissolved after 2 h of stirring. The mixture was reacted for another 16 h. The flask was equipped with a reflux condenser and contents were heated at 66° C. for 16 h. After cooling to room temperature, the reaction mixture was filtered through a sintered funnel (porosity: ~4.5-5 microns). Tetrahydrofuran (3 portions; 25 mL each) was used to wash the beads and the filtration assembly. The supernatant was combined with the filtrate. Removal of volatiles provided the title compound as a light brown cloudy solid (mercaptan equivalent weight: 429; theoretical functionality: 3.0) that contained very fine off-white solid particles.

Example 6

Synthesis of a Difunctional Reactive Antioxidant Prepared from 2,3,4-Trihydroxybenzaldehyde and DMDO

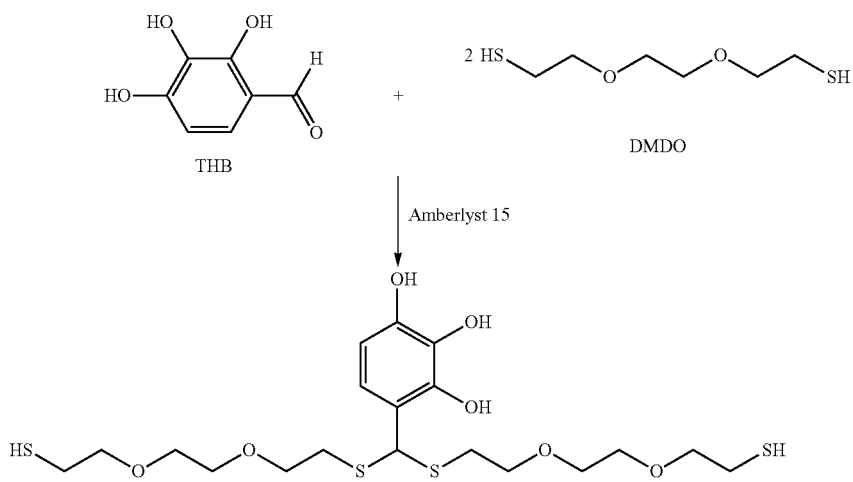

Amberlyst® 15 (0.77 g), 2,3,4-dihydroxybenzaldehyde (5.09 g; 0.033 mole) and THF (9.0 g) were charged into a 50-mL 3-necked round-bottomed flask. The flask was equipped with a magnetic stir bar and a gas adapter and a temperature probe.

Most of the aldehyde had dissolved after ½ h of stirring. DMDO (12.03 g; 0.066 moles) was added (temp.: 18.4° C.) into the heterogeneous solution with tetrahydrofuran (1.17 g). A mild exotherm started immediately and the temperature reached 34° C. in 15 min. After 20 h of additional stirring, IR analysis of the supernatant solution confirmed the absence of an aldehyde signal (1646 cm$^{-1}$).

The flask was equipped with a reflux condenser and contents were heated at 66° C. for 9 h. After cooling to room temperature, the reaction mixture was filtered through a sintered funnel (porosity: 5 micron). Removal of volatiles provided a red viscous liquid (viscosity: 574 P; theoretical functionality: 2.0). The equivalent weight could not be determined because of poor solubility. However, curing the product (on a basis of theoretical equivalent weight of 250) with an epoxy accelerator provided a cured specimen; hardness (24 h): 84 Shore A.

Comparative Example 7

Cured Sealant without an Antioxidant

Base 5312 (165 g) (PR-2001 B-2, Part B, filled thiol-terminated polythioether available from PRC-DeSoto International, Inc., 30-60 wt % thiol-terminated polythioether, 30-60 wt % calcium carbonate, 1-10 wt % aluminum hydroxide) and Epoxy S-5304 (30.53 g) (PR-2001 B-2, Part A: epoxy resin mixture available from PRC-DeSoto International, Inc.; 30-60 wt % limestone, 10-30 wt % polymer of epichlorohydrin, phenol-formaldehyde, 10-30 wt % bisphenol A/epichlorohydrin-based epoxy resin, 1-10 wt % hydrogenated terphenyl) were charged into a 200 g mixing cup. The contents were mixed (two cycles of hand mixing and mixing further in a Hauschild mixer for 30 sec) and a tensile/elongation flowout was made. After curing for 6 days/room temperature and 1 day/140° F., tensile/elongation specimens were cut from the flowout. Hardness, tensile and elongation were measured on exposed (fuel/heat) and pre-exposed specimens. Exposure cycle: fuel (immersion in JRF Type I for 3 days/140° F.); heat (3 days/120° F., 7 days/300° F. and 24 h/room temperature).

Comparative Example 8

Cured Sealant Containing Antioxidant Irganox® 1010

A solution of Irganox® 1010 (3.13 g in 3.13 g of acetone) and Base 5312 (165 g) were charged into a 200 g mixing cup. The contents were mixed in a Hauschild mixer, first for 30 sec and then for a cycle of 4 min. Epoxy S-5304 (30.53 g) was added, the contents were mixed (two cycles of hand mixing and mixing further in a Hauschild mixer for 30 sec) and a tensile/elongation flowout was made. After a cure cycle of 6 days/room temperature and 1 day/140° F., tensile/elongation specimens were cut from the flowout. Hardness, tensile and elongation were measured on exposed (fuel/heat) and unexposed specimens. Exposure cycle: fuel (immersion in JRF Type I for 3 days/140° F.); heat (3 days/120° F., 7 days/300° F. and 24 h/room temperature).

Example 9

Cured Sealant Containing Reactive Antioxidant of Example 1

Base 5312 (100 g) and the reactive antioxidant of Example 1 (10.81 g) were charged into a 200 g mixing cup and the contents mixed in a Hauschild mixer for 30 sec. The contents were hand mixed and mixed further in a Hauschild mixer for 30 sec. Epoxy S-5304 (45.46 g) was added, the contents mixed (two rounds of hand mixing and mixing further in Hauschild mixer for 30 sec), and a tensile/elongation flowout was made. After curing for 2 days/room temperature and 1 day/140° F., tensile/elongation specimens were cut from the flowout. Hardness, tensile and elongation were measured on exposed (fuel/heat) and unexposed specimens. Exposure cycle: fuel (immersion in JRF Type I for 3 days/140° F.); heat (3 days/120° F., 7 days/300° F. and 24 h/room temperature; 6 hours/400° F.).

Properties of the cured sealants of Examples 7, 8 and 9 are provided in Table 1.

TABLE 1

Properties of cured sealants.

| | Sealant Comparative Example 7 (no Antioxidant) | Sealant Comparative Example 8 (Irganox ® 1010) | Sealant Example 9 (Antioxidant: Example 1) |
|---|---|---|---|
| Hardness Pre-Exposed (Shore A) | 42 | 42 | 50 |
| Hardness Post-Exposed 7 days/300° F. (Shore A) | 50 | 47 | 56 |
| Hardness Post-Exposed 6 hours/400° F. (Shore A) | 18 | 12 | 34 |
| Tensile Pre-Exposed (PSI) | 385 | 350 | 364 |
| Tensile Post-Exposed 7 days/300° F. (PSI) | 136 | 138 | 241 |
| Tensile Post-Exposed 6 hours/400° F. (%) | 77 | 68 | 122 |
| Elongation Pre-Exposed (%) | 430 | 412 | 263 |
| Elongation Post-Exposed 7 days/300° F. (%) | 42 | 59 | 65 |
| Elongation Post-Exposed 6 hours/400° F. (%) | 31 | 80 | 112 |

The sealant of Example 9, containing the reactive antioxidant of Example 1, exhibited improved retention of hardness, tensile strength and elongation following exposure to thermal stress.

Finally, it should be noted that there are alternative ways of implementing the embodiments disclosed herein. Accordingly, the present embodiments are to be considered as illustrative and not restrictive. Furthermore, the claims are not to be limited to the details given herein, and are entitled to their full scope and equivalents thereof.

What is claimed is:

1. A reactive antioxidant, wherein the reactive antioxidant comprises a reactive antioxidant having the structure of Formula (1a), a reactive antioxidant having the structure of Formula (1b), a reactive antioxidant having the structure of Formula (1c), or a combination of any of the foregoing:

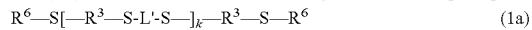

$$R^6-S[-R^3-S-L'-S-]_k-R^3-S-R^6 \tag{1a}$$

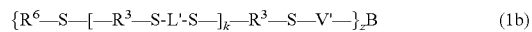

$$\{R^6-S-[-R^3-S-L'-S-]_k-R^3-S-V'-\}_zB \tag{1b}$$

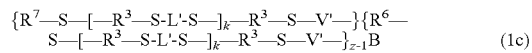

$$\{R^7-S-[-R^3-S-L'-S-]_k-R^3-S-V'-\}\{R^6-S-[-R^3-S-L'-S-]_k-R^3-S-V'-\}_{z-1}B \tag{1c}$$

wherein,
each k is independently 0 to 10, wherein at least one k is not 0;
each $R^6$ is hydrogen or comprises a moiety having a terminal reactive group;
each $R^3$ independently comprises a moiety of Formula (2):

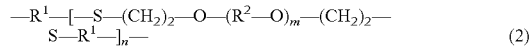

$$-R^1-[-S-(CH_2)_2-O-(R^2-O)_m-(CH_2)_2-S-R^1-]_n- \tag{2}$$

wherein,
n is an integer from 0 to 60;
each $R^1$ independently comprises $C_{2-10}$ alkanediyl, $C_{6-8}$ cycloalkanediyl, $C_{6-10}$ alkanecycloalkanediyl, $C_{5-8}$ heterocycloalkanediyl, or $-[(-CHR-)_p-X-]_q-(-CHR-)_r-$;
p is an integer from 2 to 6;
q is an integer from 1 to 5;
r is an integer from 2 to 10;
each R independently comprises hydrogen or methyl; and
each X independently comprises $-O-$, $-S-$, or $-NR-$, wherein R comprises hydrogen or methyl;
each $R^2$ independently comprises $C_{1-10}$ alkanediyl, $C_{6-8}$ cycloalkanediyl, $C_{6-14}$ alkanecycloalkanediyl, or $-[(-CHR-)_p-X-]_q-(-CHR-)_r-$, wherein p, q, r, R, and X are as defined for $R^1$; and
m is an integer from 0 to 50;
each $-L'-$ is derived from an antioxidant-containing precursor L, wherein the antioxidant-containing precursor L comprises an antioxidant moiety and at least one group reactive with a thiol group;
B represents a core of a z-valent polyfunctionalizing agent $B(-V)_z$ wherein,
z is an integer from 3 to 6; and
each $-V$ is a moiety comprising a terminal group reactive with a terminal thiol group;
each $-V'-$ is derived from the reaction of $-V$ with a thiol group; and
$R^7$ is $\{-V'-\}\{R^6-S-[-R^3-S-L'-S-]_k-R^3-S-V'-\}_{z-1}B$.

2. The reactive antioxidant of claim 1, wherein,
n is 0;
each $R^6$ is hydrogen; and
each $R^1$ is $-[(CH_2)_2-O-]_2-(CH_2)_2-$.

3. The reactive antioxidant of claim 1, wherein each -L'- comprises a moiety having the structure $-CH(-R^4)-$, wherein $R^4$ comprises an antioxidant moiety.

4. The reactive antioxidant of claim 1, wherein the antioxidant moiety comprises a hindered phenol, a hindered amine, a benzofuranone, or a combination of any of the foregoing.

5. The reactive antioxidant of claim 1, wherein L comprises a substituted benzaldehyde.

6. The reactive antioxidant of claim 1, wherein L comprises 3,5-di-tert-butyl-4-hydroxybenzaldehyde, 2,3,4-trihydroxybenzaldehyde, or a combination thereof.

7. The reactive antioxidant of claim 1, wherein,
each $R^6$ is hydrogen;
each $R^3$ is —$(CH_2)_2$—O—$(CH_2)_2$—O—$(CH_2)_2$—;
each L' is derived from a substituted benzaldehyde;
each k is 0, 1, or 2, wherein at least one k is not 0;
$B(-V)_z$ is triallyl cyanurate, wherein z is 3 and each —V is —O—$CH_2$—CH=$CH_2$; and
$R^7$ is {—V'—}{HS—[—(($CH_2)_2$—O—)$_2$—($CH_2)_2$—S-L'-S—]$_k$—(($CH_2)_2$—O—)$_2$—($CH_2)_2$—S—V'—}$_{z-1}$B.

8. A reactive antioxidant comprising a reaction product of reactants comprising:
a polythiol; and
an antioxidant-containing precursor comprising at least one group reactive with thiol groups and at least one antioxidant moiety.

9. The reactive antioxidant of claim 8, wherein,
the polythiol comprises a dithiol, a trithiol, or a combination thereof; and
the antioxidant-containing precursor comprises a substituted benzaldehyde.

10. The reactive antioxidant of claim 8, wherein the polythiol comprises a polythioether comprising the structure of Formula (10):

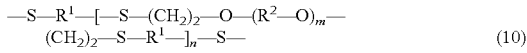
(10)

wherein,
n is an integer from 0 to 60;
each $R^1$ independently comprises $C_{2-10}$ alkanediyl, $C_{6-8}$ cycloalkanediyl, $C_{6-10}$ alkanecycloalkanediyl, $C_{5-8}$ heterocycloalkanediyl, or —[(—CHR—)$_p$—X—]$_q$—(—CHR—)$_r$—, wherein
p is an integer from 2 to 6;
q is an integer from 1 to 5;
r is an integer from 2 to 10;
each R independently comprises hydrogen or methyl; and
each X independently comprises —O—, —S—, or —NR—, wherein R comprises hydrogen or methyl;
m is 0 to 50; and
each $R^2$ independently comprises $C_{1-10}$ alkanediyl, $C_{6-8}$ cycloalkanediyl, $C_{6-14}$ alkanecycloalkanediyl, or —[(—CHR—)$_p$—X—]$_q$—(—CHR—)$_r$—, wherein p, q, r, R, and X are as defined for $R^1$.

11. The reactive antioxidant of claim 10, wherein,
n is 0; and
each $R^1$ comprises —[($CH_2)_2$—O—]$_2$—($CH_2)_2$—.

12. The reactive antioxidant of claim 8, wherein the antioxidant-containing precursor comprises 3,5-di-tert-butyl-4-hydroxybenzaldehyde, 2,3,4-trihydroxybenzaldehyde, or a combination thereof.

13. The reactive antioxidant of claim 8, wherein the polythiol comprises a thiol-terminated polythioether of Formula (7a), a thiol-terminated polythioether of Formula (7b), or a combination thereof:

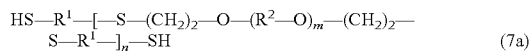
(7a)

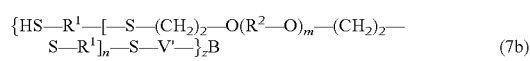
(7b)

wherein:
each $R^1$ independently comprises $C_{2-10}$ alkanediyl, $C_{6-8}$ cycloalkanediyl, $C_{6-10}$ alkanecycloalkanediyl, $C_{5-8}$ heterocycloalkanediyl, or —[(—CHR—)$_p$—X—]$_q$—(—CHR—)$_r$—, wherein:
p is an integer from 2 to 6;
q is an integer from 1 to 5;
r is an integer from 2 to 10;
each R independently comprises hydrogen or methyl; and
each X independently comprises —O—, —S—, or —NR—, wherein R is selected from hydrogen and methyl;
each $R^2$ independently comprises $C_{1-10}$ alkanediyl, $C_{6-8}$ cycloalkanediyl, $C_{6-14}$ alkanecycloalkanediyl, or —[(—CHR—)$_p$—X—]$_q$—(—CHR—)$_r$—, wherein p, q, r, R, and X are as defined for $R^1$;
m is an integer from 0 to 50;
n is an integer from 1 to 60;
B represents a core of a z-valent polyfunctionalizing agent $B(-V)_z$ wherein:
z is an integer from 3 to 6; and
each V is a moiety comprising a terminal group reactive with terminal thiol groups; and
each —V'— is derived from the reaction of —V with a thiol.

14. A composition comprising the reactive antioxidant of claim 1.

15. The composition of claim 14, further comprising a sulfur-containing prepolymer, wherein the sulfur-containing prepolymer comprises at least two terminal $R^6$ groups.

16. The composition of claim 15, wherein,
each $R^6$ is hydrogen; and
the sulfur-containing prepolymer comprises a thiol-terminated sulfur-containing prepolymer.

17. The composition of claim 16, wherein the thiol-terminated containing prepolymer comprises a thiol-terminated polythioether of Formula (7a), a thiol-terminated polythioether of Formula (7b), or a combination thereof:

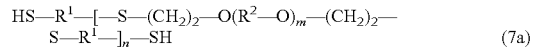
(7a)

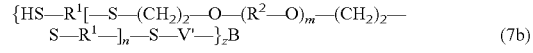
(7b)

wherein:
each $R^1$ independently comprises $C_{2-10}$ alkanediyl, $C_{6-8}$ cycloalkanediyl, $C_{6-10}$ alkanecycloalkanediyl, $C_{5-8}$ heterocycloalkanediyl, or —[(—CHR—)$_p$—X—]$_q$—(—CHR—)$_r$—, wherein:
p is an integer from 2 to 6;
q is an integer from 1 to 5;
r is an integer from 2 to 10;
each R independently comprises hydrogen or methyl; and
each X independently comprises —O—, —S—, or —NR—, wherein R is selected from hydrogen and methyl;
each $R^2$ independently comprises $C_{1-10}$ alkanediyl, $C_{6-8}$ cycloalkanediyl, $C_{6-14}$ alkanecycloalkanediyl, or —[(—CHR—)$_p$—X—]$_q$—(—CHR—)$_r$—, wherein p, q, r, R, and X are as defined for $R^1$;
m is an integer from 0 to 50;
n is an integer from 0 to 60;
B represents a core of a z-valent polyfunctionalizing agent $B(-V)_z$ wherein:
z is an integer from 3 to 6; and
each V is a moiety comprising a terminal group reactive with terminal thiol groups; and
each —V'— is derived from the reaction of —V with a thiol.

18. The composition of claim 14, comprising a curing agent, wherein the curing agent comprises a polyepoxide.

19. The composition of claim 18, formulated as a sealant.

20. A method of sealing at least a portion of a part, comprising:
- providing a curable composition comprising the composition of claim 19;
- applying the curable composition to at least a portion of a part; and
- curing the curable composition to seal at least a portion of the part.

* * * * *